(12) United States Patent
Pandya et al.

(10) Patent No.: US 11,666,576 B2
(45) Date of Patent: *Jun. 6, 2023

(54) LIQUID ORAL FORMULATIONS FOR TADALAFIL

(71) Applicant: LIQMEDS WORLDWIDE LIMITED, Hayes (GB)

(72) Inventors: Jinal Pandya, Unjha (IN); Sandip P. Mehta, Ahmedabad (IN); Manish Umrethia, Ahmedabad (IN); Jayanta Kumar Mandal, Ahmedabad (IN); Hiren Pansuriya, Ahmedabad (IN)

(73) Assignee: LIQMEDS WORLDWIDE LIMITED, Hayes (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/832,921

(22) Filed: Jun. 6, 2022

(65) Prior Publication Data

US 2022/0296602 A1 Sep. 22, 2022

Related U.S. Application Data

(63) Continuation of application No. 17/403,282, filed on Aug. 16, 2021, now Pat. No. 11,382,917, which is a continuation of application No. 16/957,894, filed as application No. PCT/IB2018/001462 on Dec. 24, 2018.

(30) Foreign Application Priority Data

Dec. 26, 2017 (IN) .............................. 201721046640
Apr. 2, 2018 (IN) .............................. 201821012438

(51) Int. Cl.
*A61K 31/4985* (2006.01)
*A61K 47/10* (2017.01)
*A61K 31/519* (2006.01)
*A61K 9/08* (2006.01)

(52) U.S. Cl.
CPC .............. *A61K 31/519* (2013.01); *A61K 9/08* (2013.01); *A61K 31/4985* (2013.01); *A61K 47/10* (2013.01)

(58) Field of Classification Search
CPC .... A61K 31/519; A61K 31/4985; A61K 9/08; A61K 47/10; A61K 31/44; A61K 31/506; A61K 31/53; A61K 9/0095; A61K 9/107; A61K 9/16
See application file for complete search history.

(56) References Cited

U.S. PATENT DOCUMENTS

| | | |
|---|---|---|
| 7,182,958 B1 | 2/2007 | Oren et al. |
| 11,337,979 B2 | 5/2022 | Pandya et al. |
| 2001/0036932 A1 | 11/2001 | Cardin et al. |
| 2003/0040514 A1 | 2/2003 | Wyllie |
| 2005/0042177 A1 | 2/2005 | Ryde et al. |
| 2005/0058710 A1 | 3/2005 | Straub et al. |
| 2006/0024335 A1 | 2/2006 | Rogers |
| 2007/0104792 A1 | 5/2007 | Jenkins |
| 2010/0184722 A1 | 7/2010 | Swart et al. |
| 2016/0279133 A1 | 9/2016 | Martinez-Alzamora |
| 2017/0049776 A1 | 2/2017 | Aboohi et al. |

FOREIGN PATENT DOCUMENTS

| | | |
|---|---|---|
| CN | 1332671 C | 8/2007 |
| CN | 106821991 A * | 6/2017 |
| CN | 106821991 A | 6/2017 |
| EP | 1097711 A2 | 5/2001 |
| IN | 20161039392 A | 5/2018 |
| SK | 87999 A3 | 1/2001 |
| WO | 200105386 A2 | 1/2001 |
| WO | 2004087211 A2 | 10/2004 |
| WO | 2005013937 A2 | 2/2005 |
| WO | 2010146407 A1 | 12/2010 |
| WO | 2012051559 A2 | 4/2012 |
| WO | 2014194872 A1 | 12/2014 |
| WO | 2017/069533 A1 | 4/2017 |

OTHER PUBLICATIONS

Hatzimouratidis, Ther. Adv. Urol., vol. 6(4), pp. 135-147, publ. 2014 (Year: 2014).*
Xu et al., English translation of CN 106821991 A, pp. 1-13, publ. Jun. 13, 2017 (Year: 2017).*
Adcirca (tadalafil) tablets prescribing information as of Feb. 8, 2011.
Cialis (tadalafil) tablets prescribing information as of Feb. 15, 2018.
Ora-Plus Product Information (2010).
Ora-Sweet Product Information (2010).
Pettit et al., Stability of an extemporaneously prepared tadalafil suspension, Am J Health Syst Pharm. 2012; 69: 592-594.
Allen, L.V., Tadalafil 5 mg/mL Oral Suspension, US Pharm. (2012) 37(5): 43-44.
Allen, L.V., Sildenafil Citrate 2.5 mg/mL Oral Liquid, US Pharm. (2018) 43(2): 47-48.
Anonymous "Revatio—Annex I Summary of Product Characteristics", Revation EMEA/H/C/000638—T/0082: 1-102 (2009).
Badwan et al., Sildenafil Citrate, Anal. Profiles Drug. Subst. (2001) 27: 339-376.
Handbook of Pharm Excipients, publ. 2005, Pharmaceutical Press, 5th ed., pp. 1-6 (2005).
Handbook of Pharmaceutical Excipients, Pharmaceutical Press, Rowe et al. Eds., 5th ed. (2005), pp. 18-20.

(Continued)

*Primary Examiner* — Sarah Pihonak
(74) *Attorney, Agent, or Firm* — Merchant & Gould P.C.; Daniel R. Evans

(57) ABSTRACT

The present disclosure is directed to pharmaceutical compositions comprising a PDE V inhibitor and one or more pharmaceutical excipients or additives wherein the pharmaceutical compositions are in the form of liquid pharmaceutical compositions. The pharmaceutical compositions of the present disclosure are useful for the treatment of diseases or conditions which are treatable by administration of PDE V inhibitor drug such as pulmonary arterial hypertension, erectile dysfunction, etc.

30 Claims, No Drawings

(56) References Cited

OTHER PUBLICATIONS

Huddleston et al, Sildenafil for the treatment of pulmonary hypertension in pediatric patients, Pediatr. Cardiol. (2009) 30 871-872.

International Search Report and Written Opinion for PCT/IB2018/001462 (dated Jun. 14, 2019).

Nahata et al., Extemporaneous sildenafil citrate oral suspensions for the treatment of pulmonary hypertension in children, Am. J. Health-Syst. Pharm. (2006) 63(3): 254-257.

Provenza et al., Design and physicochemical stability studies of paediatric oral formulations of sildenafil, Int J Pharm (2014) 460(1-2): 234-239.

Reddy et al., International J. Pharmacy, pub. 2016, vol. 6(3). pp. 137-142 (2016).

Revatio (sildenafil) tablets prescribing information as of Jul. 31, 2007.

The EMEA CHMP Assessment Report for Vizarsin (International Nonproprietary Name: Sildenafil) (2009).

Viagra (sildenafil citrate) tablets prescribing information as of Jul. 8, 2005.

* cited by examiner

LIQUID ORAL FORMULATIONS FOR TADALAFIL

RELATED APPLICATIONS

This application is a continuation of U.S. patent application Ser. No. 17/403,282, filed on Aug. 16, 2021, now U.S. Pat. No. 11,382,917 B2, which is a continuation of U.S. patent application Ser. No. 16/957,894, filed on Jun. 25, 2020, now U.S. Pat. No. 11,464,778 B2, which is the U.S. National Stage Application of PCT/M2018/001462, filed on Dec. 24, 2018, which claims priority to Indian Patent Application No. IN201721046640, filed on Dec. 26, 2017, and Indian Patent Application No. IN201821012438, filed on Apr. 2, 2018, where each application is incorporated herein by reference.

FIELD

The present disclosure relates, in general, to the pharmaceutical field, and more precisely it relates to the pharmaceutical compositions comprising PDE V inhibitors. In particular, the present disclosure relates to the liquid compositions comprising PDE V inhibitors e.g. sildenafil, tadalafil, or sildenafil citrate. The pharmaceutical compositions disclosed herein may be useful for treating pulmonary arterial hypertension and/or diseases in which PDE V inhibitors have been found as effective therapy for, for example, male erectile dysfunction.

SUMMARY

Embodiments herein are directed to liquid oral formulations of PDE V inhibitors. In some embodiments, a liquid pharmaceutical composition of a PDE V inhibitor drug comprises a PDE V inhibitor drug or a derivative thereof and a wetting agent, wherein the pH of the pharmaceutical composition is about 4 to about 8. In some embodiments, the pharmaceutical composition further comprises one or more pharmaceutically acceptable excipients selected from the group consisting of vehicles, solvents/co-solvents, solubilizers, solubility enhancing agents, viscosity modifying agents, permeation/penetration enhancers, tonicity agents, mucoadhesives, bulking agents/auxiliary suspending agents, chelating agents, wetting agents, anti-foaming agents, anti-caking agents, stabilizing agents, anti-oxidants, pH modifying agents and/or pH adjusting agents, surfactants, preservatives, sweetening agents, flavoring agents and coloring agents and combination thereof. In some embodiments, the one or more pharmaceutically acceptable excipients is a buffering agent. In some embodiments, the pharmaceutical composition is a suspension, wherein the wetting agent is glycerin. In some embodiments, the glycerin to buffering agent ratio in the pharmaceutical composition is about 40:60. In some embodiments, the buffering agent is in an amount suitable to make the composition pH about 4 to about 8. In some embodiments, the liquid pharmaceutical composition may be in the form of a solution or a suspension. In some embodiments, the pharmaceutical composition is a suspension further comprising a viscosity modifying agent.

In some embodiments, the PDE V inhibitor drug is selected from the group comprising of Avanafil, AWD-12-250, BF/GP-385, BMS-22313, BMS-341400, CP-248, CP-461, DA-8159, Dasantafil, DMPPO, E-4021, E-8010, EMD-82639, EMR-62203, Exisulind, FR-181074, FR-226807, FR-229934, GF-248, KF-31327, KT-734, LAS-34 179, Lusupultide, MJ-12504, NCX-91 1, NM-702, OPC-35564, OSI-461, QAD-171A, Roflumilast, SB-96231, SCH-46642, SCH-51866, SCH-59498, Sildenafil, Sildenafil citrate, SK-350, SK-3530, SKF-96231, Sophoflavescenol, SR-265579, T-0156, T-1032, Tadalafil, UK-1 14502, UK-1 14542, UK-357903, UK-369003, UK-371800, UK-83405, Vardenafil, WIN-65579, WS-63967, YC-1 and Zaprinast, or pharmaceutically acceptable salts, chemical derivatives such as polymorphs, solvates, hydrates, anhydrous forms, amorphous forms, prodrugs, racemic mixtures or pure forms, chelates, and complexes thereof. In some embodiments, the PDE V inhibitor drug is sildenafil. In some embodiments, the PDE V inhibitor drug is sildenafil citrate. In some embodiments, the PDE V inhibitor drug is tadalafil.

Some embodiments are directed to the use of a liquid pharmaceutical composition according to an embodiment herein in the treatment of at least one disease or condition selected from the group comprising of hypertension, pulmonary hypertension, arterial hypertension, pulmonary arterial hypertension, erectile dysfunction, cirrhosis, solid tumor, heart failure, cerebral vasospasm, arthritis, rheumatoid arthritis, atherosclerosis, congenital heart diseases, Parkinson's disease, neonatal encephalopathy, pre-eclampsia, prostate cancer, pancreatic cancer, hepatic encephalopathy, aortic stenosis, cystic fibrosis, peripheral arterial occlusive disease, sickle cell disease, priapism, age-related macular degeneration, schizophrenia, bronchopulmonary dysplasia, impotence, lymphangioma, dysmenorrhea, urinary incontinence, chronic obstructive pulmonary disease, lymphatic malformations, Duchenne muscular dystrophy, Becker muscular dystrophy, pulmonary fibrosis, nontuberculous mycobacterial infection, idiopathic pulmonary fibrosis, Raynaud's phenomenon, prostatic hyperplasia, benign prostatic hyperplasia Waldenstrom's macroglobulinemia and any combination thereof.

DETAILED DESCRIPTION

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only, and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein is not entitled to antedate such disclosure by virtue of prior invention.

Definitions

It must also be noted that as used herein and in the appended claims, the singular forms "a," "an," and "the" include plural reference unless the context clearly dictates otherwise. Thus, for example, reference to a "surfactant" is a reference to one or more surfactants and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with an active pharmaceutical ingredient, can include, but is not limited to, providing the active pharmaceutical ingredient into or onto the target tissue; providing the active pharmaceutical ingredient systemically to a patient by, e.g., intravenous injection whereby the therapeutic reaches the target tissue; providing the active pharmaceutical ingredient in the form of the encoding sequence thereof to the target tissue. "Administering" a composition may be accomplished by injection, topical administration, orally, or by either method in combination with other known techniques. In some embodiments, administering is through an oral route of administration.

The term "subject" as used herein includes, but is not limited to, humans and non-human vertebrates such as wild, domestic, and farm animals. In certain embodiments, the subject described herein is an animal. In certain embodiments, the subject is a mammal. In certain embodiments, the subject is a human. In certain embodiments, the subject is a non-human animal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The term "improve" is used to convey that the compounds of embodiments herein change either the appearance, form, characteristics and/or the physical attributes of the tissue to which it is being provided, applied or administered. In some embodiments, the pharmaceutical compositions of embodiments herein comprising sildenafil for male erectile dysfunction.

The term "inhibit" includes the administration of a compound of embodiments herein to prevent the onset of the symptoms, alleviating the symptoms, or eliminating the disease, condition or disorder. In some embodiments, the pharmaceutical compositions of embodiments herein comprising a sildenafil are used to inhibit symptoms of pulmonary arterial hypertension.

By "pharmaceutically acceptable", it is meant the carrier, diluent or excipient must be compatible with the other ingredients of the formulation and not deleterious to the recipient thereof.

The term "pharmaceutically acceptable excipients" as used herein refers to such pharmaceutically acceptable excipients which are known to those skilled in the art for the purposes of preparing liquid pharmaceutical compositions of the present disclosure. Such pharmaceutically acceptable excipients, without limitation include, vehicles, solvents/co-solvents, solubilizers, solubility enhancing agents, tonicity agents, permeation/penetration enhancers, mucoadhesives, viscosity modifying agents, bulking agents/auxiliary suspending agents, wetting agents, anti-foaming agents, anti-caking agents, stabilizing agents, anti-oxidants, chelating agents, buffering agents/pH modifying agents/pH adjusting agents, surfactants, preservatives, sweetening agents, flavoring agents and the like or any combination thereof. Such pharmaceutically acceptable excipients can be used in an amount which provides the liquid pharmaceutical compositions of the present disclosure desired property for which they are intended or desired to use.

As used herein, the terms "stable" or "stability" encompass any characteristic of the liquid compositions which may be affected by storage conditions including, without limitation, potency, total impurities, degradation products, specific optical rotation, optical purity, water content, appearance, viscosity, sterility, and colour and clarity. The storage conditions which may affect stability include, for example, duration of storage, temperature, humidity, and/or light exposure.

As used herein, the term "therapeutic" means an agent utilized to treat, combat, inhibit, ameliorate, prevent or improve an unwanted condition or disease of a patient. In part, the pharmaceutical compositions of embodiments herein are directed to the treatment of male erectile dysfunction.

A "therapeutically effective amount" or "effective amount" of a composition is a predetermined amount calculated to achieve the desired effect. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, concomitant therapies and the condition being treated. However, it will be understood that the effective amount administered will be determined by the physician in the light of the relevant circumstances including the condition to be treated, the choice of compound to be administered, and the chosen route of administration, and therefore the above dosage ranges are not intended to limit the scope of embodiments herein in any way. A therapeutically effective amount of a compound of this disclosure is typically an amount such that when it is administered in a physiologically tolerable excipient composition, it is sufficient to achieve an effective systemic concentration or local concentration in the tissue.

The terms "treat," "treated," or "treating," as used herein, refers to both therapeutic treatment and prophylactic or preventative measures, wherein the object is to inhibit, prevent or slow down (lessen) an undesired physiological condition, disorder or disease, or to improve, inhibit, or otherwise obtain beneficial or desired clinical results. For the purposes of this invention, beneficial or desired clinical results include, but are not limited to, improvement or alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

As used herein, the term "a derivative thereof" refers to a salt thereof, a pharmaceutically acceptable salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof. In some embodiments, the active pharmaceutical ingredient may be administered as a derivative thereof. In some embodiments, reference to a derivative, e.g. a salt thereof, shall be interchangeable with the active pharmaceutical ingredient or any other derivative thereof. For example, unless otherwise stated, sildenafil and sildenafil citrate may be used interchangeably herein.

In embodiments or claims where the term "comprising" is used as the transition phrase, such embodiments can also be envisioned with replacement of the term "comprising" with the terms "consisting of or "consisting essentially of."

As used herein, the term "consists of or "consisting of means that the composition, formulation or the method includes only the elements, steps, or ingredients specifically recited in the particular claimed embodiment or claim.

As used herein, the term "consisting essentially of or "consists essentially of means that the composition, formulation or the method includes only the elements, steps or ingredients specifically recited in the particular claimed embodiment or claim and may optionally include additional elements, steps or ingredients that do not materially affect the basic and novel characteristics of the particular embodiment or claim. For example, the only active pharmaceutical ingredient(s) in the formulation or method that treats the specified condition (e.g. seizures) is the specifically recited therapeutic(s) in the particular embodiment or claim.

PDE V Inhibitors

A phosphodiesterase type V inhibitor (PDE V inhibitor) is a drug used to block the degradative action of cGMP-specific phosphodiesterase type V (PDE V) on cyclic GMP in the smooth muscle cells lining the blood vessels supplying the corpus cavernosum of the penis. These drugs are used in the treatment of erectile dysfunction and were the first effective oral treatment available for the condition. Because PDE V is also present in the arterial wall of smooth muscle within the lungs, PDE V inhibitors have also been explored for the treatment of pulmonary arterial hypertension, a disease in which blood vessels in the lungs become overloaded with fluid, usually as a result of failure of the right ventricle of the heart.

Sildenafil is a drug belonging to the group of selective inhibitors of phosphodiesterase-V (PDE V), an enzyme that is responsible for the degradation of cyclic guanosine monophosphate (GMPc), such that the Sildenafil promotes an increase in GMPc levels, which in turn promotes the relaxation of smooth muscle tissue.

The PDE V enzyme is present, for example, in the pulmonary vasculature, such that Sildenafil induces an increase in GMPc in the cells of the lungs' smooth muscle vasculature, which has a therapeutic application in patients affected by pulmonary hypertension due to its vasodilatory effect on the pulmonary vascular bed and on systemic circulation.

This enzyme is also present in the corpora cavernosa in the penis, Sildenafil is, therefore, used in the treatment of erectile dysfunction, as an increase in GMPc levels causes the relaxation of the smooth muscles in the erectile tissue of these corpora cavernosa, allowing blood to flow into its interior, thereby promoting an erection.

The USFDA approved Sildenafil for the treatment of Pulmonary Arterial Hypertension (PAH) in 2005. It is marketed for PAH as REVATIO®. In 2009, USFDA also approved Tadalafil, another PDE V inhibitor, marketed under the name ADCIRCA®. PDE V inhibitors are believed to increase pulmonary artery vasodilation, and inhibit vascular remodeling, thus lowering pulmonary arterial pressure and pulmonary vascular resistance.

REVATIO® manufactured by Pfizer Pharmaceuticals is most often supplied as 20 mg tablets to be taken 3 times daily. Sildenafil citrate is often labeled with the amount of Sildenafil so that the actual amount of Sildenafil citrate is about 30% more than the dosage/tablet indicated on the label.

REVATIO® is also available in injectable form as a clear colorless, sterile, and ready to use solution containing 10 mg of Sildenafil citrate per 12.5 ml of solution. Each ml of solution contains 1.124 mg sildenafil citrate, 50.5 mg dextrose and water for injection. The injectable form of REVATIO® is most often administered intravenously. This route of administration is practical in a hospital setting but impractical outside a 20 hospital or clinic setting.

REVATIO® (Sildenafil citrate) is also available as powder for oral suspension (POS) at a concentration of 10 mg/ml. REVATIO® POS is supplied by Pfizer to be made up into an oral suspension. Additional ingredients in the POS include colloidal silicon dioxide, sucralose, sorbitol, sodium benzoate, sodium citrate, flavor and xanthan gum. The active ingredient in suspension has a slower absorption rate than would be expected for a solution with a similar concentration. In addition, the presence of some of the additional ingredients makes this product difficult to tolerate for people with known sensitivities to these ingredients.

Whether provided as tablets or oral suspension, Sildenafil citrate exhibits an absolute bioavailability of about 41% and is reported to result in maximum observed plasma concentrations within 30 to 120 minutes following oral dosing in a fasted state. The rate of absorption is reportedly reduced if taken with a high fat meal.

According to the US package insert for VIAGRA®, solubility of Sildenafil citrate in water is 3.5 mg/ml. The EMEA CHMP Assessment Report for Vizarsin (International Nonproprietary Name: Sildenafil) indicates that it is insoluble in ethanol, chloroform and acetone but soluble in methanol and dimethylsulfoxide (DMSO). The Jordanian Pharmaceutical Manufacturing Co. reports that Sildenafil citrate is about 3.5 times less soluble in ethanol than in water (~1 mg/ml). The low water solubility of Sildenafil citrate and/or its high pre-systemic elimination each independently contribute to its low oral bioavailability.

Tadalafil is an active ingredient of an erectile dysfunction medicament that is well-known under the trade name CIALIS®. Tadalafil is a selective and reversible inhibitor for cGMP-specific PDE V (phosphodiesterase type V). When nitrogen oxide is locally released due to sexual arousal, the level of cGMP is increased in the corpus cavernosum due to the inhibition of PDE V by Tadalafil. When the level of cGMP is increased in this way, smooth muscle relaxation and blood inflow to the penile tissue may result, thus causing an erection. Tadalafil has also been approved by the USFDA for the treatment of pulmonary arterial hypertension to improve exercise ability under the trade name of ADCIRCA®.

When tadalafil is absorbed via oral administration, the average time required to reach the maximum blood concentration (Cmax) is reported to be 2 hours. Thereby, Tadalafil is recommended to be taken at least 30 min prior to a sexual act. However, waiting 30 min before sex is regarded as very awkward to users.

Also, tadalafil exhibits a very low bioavailability of 20.5% when measured using rats upon intravenous administration. Such a low bioavailability results from very low solubility of Tadalafil, and concretely, Tadalafil merely has a water solubility of about 2 μg/mL.

Because of the low solubility of tadalafil, tadalafil is substantially a poorly soluble drug. Since a drug that is orally administered is absorbed only in an amount that can be dissolved in gastrointestinal tract fluids, the bioavailability of tadalafil is considerably low.

Children generally reject taking medicine which does not have a favorable shape, taste, flavor, etc. However, if a child who needs to take a medicine, rejects taking it, he might never recover from his condition. When a child is unable to take medicine orally, it is intravenously administered, and he and his caregivers then may experience stress. Syrups and suspensions are considered as favorable types of dosage forms in which to orally administer medicine to infants and children. However, they may have disadvantages such as solubility, a bad taste, portability problems or required refrigerator storage. World Health Organization (WHO) currently favors that infants and children be treated with oral solid medicines. New oral solid tablets, such as a minitablet, instead of liquid medicines are proposed for this group, however, there are a few reports that mini-tablets are suitable for infants and children. Palatability is one of the main elements of patient acceptability of an oral pediatric medicine. Palatability is defined as the overall appreciation of an oral medicinal product in relation to its smell, taste, aftertaste and feeling in the mouth. Design of the formulation of an oral pediatric medicine should be considered together with its palatability.

Compared to conventional tablets and capsules, oral liquid dosage forms including solutions, syrups, suspensions, elixirs, and concentrates offer unique advantages to many patients. For example, liquids may provide better patient compliance for those with swallowing difficulties and better dosage control versus a fixed tablet dose. Hence, liquid dosage forms are generally formulated for use in geriatric and pediatric patients. However, there are also a number of "challenges" surrounding the formulation and development of these forms.

Oral liquids are formulated as solutions, suspensions and emulsions depending on the nature of the active ingredient particularly solubility and stability. They are also designed as ready to use liquids and powders for reconstitution into liquid orals like syrups, solutions, suspensions and emulsions. Liquid formulation needs various excipients including vehicle, solubilizer, stabilizer, and viscosity builder, preservative and off course sweeteners, color and flavor. The selection of these excipients is of major concern to design stable, effective and palatable oral liquid formulation.

Characteristics of active drug are of major concern in developing an oral liquid dosage formulation. The major challenges in developing oral liquid dosage forms are (i) the stability of a drug in solution, (ii) the solubility of a drug at the required level, and (iii) an acceptable taste. It is the effective use of excipients, which allows formulators overcome these challenges. Additionally, an excipient's compatibility with a drug in the solid state cannot infer the same compatibility in solution.

The decision to develop a solution, syrup or a suspension of a drug is influenced by many factors like solubility and the desired release profile of the drug and properties of the base vehicle like surface tension, viscosity, boiling point, and specific heat of solution, all of which may be affected in various ways. In case of clear liquids, lack of solubility of the drug in the base vehicle may demand the need for miscible co-solvents. Similarly, a miscible solvent may be needed to decrease the solubility of the drug in a primary vehicle in formulating a suspension.

The therapeutic utility of drugs involves the application of dosage forms/delivery systems, which serve as carrier systems together with several excipients to deliver the active therapeutic agent to the site of action. Suspensions are an important class of pharmaceutical dosage forms that may be given by many routes, including oral, topical, parenteral, and also used in the eye for ophthalmic purposes. Surprisingly, large proportions of new drug candidates that are emerging are predominantly water insoluble and, therefore, demonstrate poor bioavailability in the solution dosage form. While suspensions present a viable formulation option for many drugs, particularly for water insoluble, hydrophobic drug substances, there are certain criteria that a well-formulated suspension should meet.

The suspension dosage form has long been used for poorly soluble active ingredients for various therapeutic indications. Development of stable suspensions over the shelf life of the drug product continues to be a challenge on many fronts. Drugs from suspension formulations typically exhibit an improved bioavailability when compared to the same drug formulated as a tablet or capsule.

A good understanding of the fundamentals of dispersion systems is essential in the development of a suitable pharmaceutical suspension. The development of a suspension dosage form follows a very complicated path. The selection of the proper excipients (surfactants, viscosity imparting agents etc.) is important. The particle size distribution in the finished drug product dosage form is a critical parameter that significantly impacts the bioavailability and pharmacokinetics of the product.

Suspensions are an important class of pharmaceutical dosage forms. The advantages of suspension dosage forms include effective dispensing of hydrophobic drugs; avoidance of the use of co-solvents; masking of unpleasant taste of certain ingredients; offering resistance to degradation of drugs due to hydrolysis, oxidation or microbial activity; easy swallowing for young or elderly patients; and efficient intramuscular depot therapy. In addition, when compared to solution dosage forms, relatively higher concentration of drugs can be incorporated into suspension products. To date, numerous theories have been introduced and successfully used to explain the unique behavior of suspension preparations.

Ready to use liquid compositions of PDE V inhibitors are not much explored in the prior art. REVATIO® is a powder for oral suspension (POS) and not a ready to use liquid composition. REVATIO® POS requires that it be mixed with water in order to prepare a suspension before use. Reconstitution of the powder for oral suspension comprises following steps (retrieved from the USFDA prescribing information of REVATIO®; www.accessdata.fda.gov/drugsatfda_docs/label/2017/203109s0l 1,022473s0l 1, 021845s020lbl.pdf):

1. Tap the bottle to release the powder.
2. Remove the cap.
3. Accurately measure out 60 mL of water and pour the water into the bottle.
4. Replace the cap and shake the bottle vigorously for a minimum of 30 seconds.

5. Remove the cap.
6. Accurately measure out another 30 mL of water and add this to the bottle. You should always add a total of 90 mL of water irrespective of the dose prescribed.
7. Replace the cap and shake the bottle vigorously for a minimum of 30 seconds.
8. Remove the cap.
9. Press the bottle adaptor into the neck of the bottle. The adaptor is provided so that you can fill the oral syringe with medicine from the bottle. Replace the cap on the bottle.
10. Write the expiration date of the constituted oral suspension on the bottle label (the expiration date of the constituted oral suspension is 60 days from the date of constitution).

It is therefore very difficult for a patient or caregiver to prepare the oral suspension by following the above mentioned process and therefore it has to be prepared by a healthcare provider. Further, such preparation is a time consuming process and the patient cannot be benefited by immediate dose as and when required. The need therefore exists in the art for the preparation of ready to use, liquid compositions comprising PDE V inhibitors. Such ready to use, liquid compositions help in avoiding the time consuming process required for preparing oral suspension. Further, preparation of oral suspension requires expertise (e.g. accurate measuring of water, shaking of the bottle in proper manner, removal of foams & clumps from the suspension) and is therefore difficult for the patient or caregiver to prepare oral suspension.

Other known compositions comprise excipients which are either additional for the formulations or not good when used for human consumption, say for example alcohol based formulations. It would therefore be desirable to have liquid compositions of PDE V inhibitors such as sildenafil, tadalafil or pharmaceutically acceptable salts thereof available which are Because of their liquid character, liquid compositions represent an ideal dosage form for patients who have difficulty swallowing tablets or capsules. This factor is of particular importance in administration of drugs to children and aged patients. The present disclosure is directed to liquid pharmaceutical compositions of PDE V inhibitors. The liquid compositions of the present disclosure are useful for administering to pediatric and geriatric patients. The liquid pharmaceutical compositions according to the present disclosure include liquids, liquid dispersions, suspensions, solutions, emulsions, sprays, spot-on, syrups, elixirs, drops, concentrates and the like.

Most PDE V inhibitors are bitter in taste and are therefore not acceptable to some patient populations such as the pediatric population. Bitter taste of the drugs can be masked by preparing liquid dosage forms such as solutions or suspensions which comprise sweeteners as well as flavors. Acceptability of dosage forms comprising PDE V inhibitor drugs can thus be increased by increasing its palatability. Therefore, the present disclosure provides liquid pharmaceutical compositions of PDE V inhibitor drugs having palatability.

Liquid dosage forms are designed as ready to use liquids and as powder for reconstitution into liquid orals like syrups, solutions, suspensions and emulsions. As discussed in above paragraphs, powder for reconstitution may require skills & expertise and needs to be prepared by a healthcare provider and may not be prepared by the patient or caregiver. The reconstitution process may also be a time consuming process and the patient cannot be benefited by the immediate dose of drug as and when required. In such a situation, ready to use, liquid compositions of PDE V inhibitor drug may be very useful and the patients can be given required doses immediately using ready to use, liquid compositions of PDE V inhibitor drug. Therefore, the present disclosure provides a ready to use, liquid pharmaceutical compositions of PDE V inhibitor drug.

The solution dosage form can be a viable alternative for patients who have problems in swallowing the tablet or capsule dosage form. It provides assurance of dosage uniformity upon administration to patients and eliminates difficulty of administration. A solution can also provide physicians more flexibility in designing dosage regimens for patients. Solution dosage form of PDE V inhibitor drug is suitable for administration to both pediatric and geriatric patients while also compensating for a good organoleptic properties and remaining suitably stable. Hence, the development of a liquid formulation is desirable since it offers improved patient compliance. Embodiments of the present disclosure are directed to developing solution dosage forms of PDE V inhibitor drug. The solution dosage forms according to the present disclosure comprises PDE V inhibitor drug or pharmaceutically acceptable salt thereof and one or more pharmaceutically acceptable excipients or additives selected from the group comprising of vehicles, solvents/co-solvents, solubilizers, surfactants, pH adjusting agents and/or pH modifying agents and/or buffering agents or any combination thereof. The solution dosage forms according to the present disclosure may further comprise one or more agents selected from the group comprising of preservatives, sweetening agents, flavoring agents and coloring agents or any combination thereof.

Suspensions possess certain advantages over other liquid dosage forms. Some drugs are insoluble in all acceptable media and must, therefore, be administered as a tablet, capsule, or as a suspension. In addition, disagreeable tastes can be masked by a suspension of the drug or a derivative of the drug. Drugs in suspension are chemically more stable than in solution.

Oral administration of drug is considered to be the most important and convenient method for maximum effectiveness of the drug molecules. Liquid dosage form is the most common and widely accepted dosage form for having advantages such as faster absorption than solid, palatable, better choice especially for children and old age patients, more flexibility in achieving the proper dosage of medication and provides ease for the patients having difficulty in swallowing other oral dosage forms. Further, pharmaceutical agents are known to have strong bitterness which results into a bitter taste and a feeling of numbness in the mouth. Therefore oral solid dosage forms are not preferred for some types of patient population.

An important consideration in any treatment regime is to ensure that the patient receives the correct dose of medicine. For many patients and many drugs there is an acceptable dose window that allows fixed-dose medicines to be used to treat patients with a wide range of body weights without the need to precisely adjust the dose. However, there are other groups of patients where the "fixed-unit-dose" model may not be appropriate, depending on the drug's therapeutic index and pharmacokinetics, e.g. pediatric patients, geriatric patients, patients with severe renal insufficiency and patients with severe hepatic insufficiency. Oral solid unit dose forms, e.g. tablets and capsules, are not convenient under such circumstances since they are fixed strength unit dose forms.

In contrast, oral liquid dose forms do have the in-built flexibility that allows the dose to be tailored to the patients' needs.

Where the drug is sufficiently soluble, a solution dosage form, e.g. a simple mixture, may be used. But not all drugs are sufficiently soluble to allow suitable strength solution medicines to be developed and manufactured with an acceptable shelf-life. In such cases, an alternative approach could be to develop a stable aqueous suspension that will allow consistent dosing of the patient. Pharmaceutical suspensions have several advantages and disadvantages when compared to other dosage forms. Since suspensions are liquids, dose adjustment for patients with renal or hepatic impairment, or for pediatric or geriatric patients, may be more straightforward. This is an oversimplification of the development of a dosing strategy for a drug candidate. There are many other details that must be considered for a formulation development project to be successful, but it does provide a simple overview of some of the issues.

The suspension must be physically stable (no appreciable settling) for a sufficient time, chemically stable over the required time (shelf-life), possess a viscosity that allows it to be used for its intended purpose, be easily reconstituted by shaking, and be acceptable in use to the patient, care-giver or other user.

Some materials may possess a combination of properties useful in the formulation and manufacture of stable, elegant pharmaceutical suspensions. Formulation scientists need to consider the totality of properties possessed by a particular excipient. Even though it is being added for one particular characteristic, the other properties will still be present, and will still influence the formulation.

Many of the recently discovered active pharmaceutical ingredients are quite hydrophobic with limited solubility. They may also be quite distasteful. Other drugs may also have quite a high chemical degradation precluding them to be administered as aqueous solutions, and in this case, it may be possible to synthesize an insoluble derivative. In other cases, some drugs are required to be present in the gastro-intestinal tract or in the pre-corneal pocket with long residence time. For such drugs, a suspension is an ideal delivery system as it provides better chemical stability and larger surface area and is often more bioavailable than aqueous solutions, tablets, and capsules.

Formulation of an elegant, stable, preserved, safe, and effective suspension is a technically challenging task compared aqueous solutions, tablets, and capsules. Pharmaceutical suspensions are thermodynamically unstable systems. Thus, preparation of such systems is often associated with problems of physical stability, content uniformity, sedimentation, caking, re-suspendability, and crystal growth. Furthermore, issues related to the masking of bitter taste and undesirable odor of the pharmaceutical ingredient must be taken into consideration.

Some desirable attributes of a suspension are described as follows,
1. It should be safe, effective, stable, and pharmaceutically elegant during the shelf life of the product.
2. The drug should not have a quick sedimentation rate. Furthermore, it should re-suspend easily upon shaking and it must not cake.
3. Physical attributes such as particle size, particle size distribution, viscosity should remain fairly uniform throughout the shelf life of the product.
4. Its viscosity must promote free and uniform flow from the container. The product must have appropriate substantivity that it spreads freely over the affected area.
5. Re-suspension should produce a homogeneous mix of drug particles such that there is a content uniformity with each dose.

A quick means to identify whether or not a drug may be more suitable for solution or suspension is to overlap the pH-stability profile with the pH-solubility profile. This overlap creates a window, which may suggest which dosage form might be most desirable and subsequently the type of excipients needed.

Oral liquid formulation needs a meticulous blend of ingredients to perform various functions like wetting and solubilization, stabilization and to impart suitable color, taste and viscosity. The blend should be compatible, non-reactive and stable. The common excipients generally required for any liquid formulation are vehicles (base), viscosity builders, stabilizers, preservatives, colors and flavors. In addition, solubilizers are required in case of clear liquids, viscosity modifying agents are needed for suspensions and emulsifying agents for emulsions.

The solution dosage form can be a viable alternative for patients who have problems in swallowing the tablet or capsule dosage form. It provides assurance of dosage uniformity upon administration to patients and eliminates difficulty of administration. A solution can also provide physicians more flexibility in designing dosage regimens for patients. Solution dosage forms of PDE V inhibitor drugs are suitable for administration to both pediatric and geriatric patients while also compensating for a good organoleptic properties and remaining suitably stable. The development of a liquid formulation is therefore desirable since it offers improved patient compliance.

Suspensions possess certain advantages over other liquid dosage forms. Some drugs are insoluble in all acceptable media and must, therefore, be administered as a tablet, capsule, or as a suspension. In addition, disagreeable tastes can be masked by a suspension of the drug or a derivative of the drug. Drugs in suspension are chemically more stable than in solution.

Liquid dosage forms may be designed as ready to use liquids and as powder for reconstitution into liquid orals like syrups, solutions, suspensions and emulsions. Powder for reconstitution may require skills and expertise and, thus, may need to be prepared by a healthcare provider. The reconstitution process may also be time consuming and the patient may not be benefited by having the immediate dose of PDE V inhibitor drug when required. In such a situation, ready to use, liquid compositions of PDE V inhibitor drug may be very useful and the patients can be given required doses immediately using ready to use, liquid compositions of PDE V inhibitor drug.

Liquid Oral Formulations

Embodiments of the present disclosure therefore provide suspension dosage forms of PDE V inhibitor drug. The suspension dosage forms according to the present disclosure comprises PDE V inhibitor drug or pharmaceutically acceptable salt thereof and one or more pharmaceutically acceptable excipients or additives selected from the group comprising of vehicles, solvents/co-solvents, solubilizers, viscosity modifying agents, anti-foaming agents, anti-caking agents, wetting agents, surfactants, pH adjusting agents and/or pH modifying agents and/or buffering agents or any combination thereof. The suspension dosage forms according to the present disclosure may further comprise one or more agents selected from the group comprising of preservatives, sweetening agents, flavoring agents and coloring agents or any combination thereof.

Embodiments of the present disclosure are directed to providing liquid pharmaceutical compositions of PDE V inhibitor drugs comprising one or more pharmaceutically acceptable excipients or additives selected from the group comprising of vehicles, solvents/co-solvents/solubilizers/ solubilizing agents, solubility enhancing agents, tonicity agents, penetration/permeation enhancers, mucoadhesives, preservatives, pH adjusting agents/pH modifying agents/ buffering agents, surfactants, anti-foaming agents, viscosity modifying agents, bulking agents/auxiliary suspending agents, wetting agents, anti-oxidants, chelating agents, anti-caking agents, sweetening agents, flavoring agents, coloring agents and the like or any combination thereof.

In some embodiments, the present disclosure provides liquid pharmaceutical compositions comprising a PDE V inhibitor drug or a derivative thereof and one or more pharmaceutically acceptable excipients.

As discussed above, because the PDE V inhibitor or derivatives thereof herein have poor wettability (i.e. log P>2.5) in their base form, it is difficult to make liquid oral compositions of the actives. Accordingly, in some embodiments, the pharmaceutical composition further comprises a wetting agent. In some embodiments, the wetting agent is glycerin.

In some embodiments, the pharmaceutical composition is in the form of a suspension for oral delivery. In some embodiments, the pharmaceutical composition is a suspension comprising a PDE V inhibitor and glycerin, wherein the pH of the composition is about 4.0 to about 8.0. Surprisingly, it has been found that use of glycerin as the wetting agent causes the PDE V inhibitor or derivatives thereof to be easily dispersible, without being solubilized, allowing for a stable suspension to be made. Additionally, it was found that having a buffering agent which helped maintain the pH of the formulation at about 4.0 to about 8.0 helped reduce the sedimentation rate and lumpiness of the formulation.

In some embodiments, the suspension comprises active pharmaceutical ingredient or a derivative thereof, water, a viscosity modifying agent, a buffering agent in an amount sufficient to make the composition pH about 4 to about 8, and about 200 mg/mL to about 400 mg/mL glycerin. Exemplary active pharmaceutical ingredients herein may be selected from sildenafil, tadalafil, and sildenafil citrate.

In some embodiments, the pharmaceutical composition further comprises a buffering agent. In some embodiments, the ratio of glycerin to buffering agent is about 40:60. In some embodiments, the buffering agent is in an amount sufficient to make the pH of the pharmaceutical composition about 4 to about 8.

In some embodiments, the suspension comprises sildenafil or sildenafil citrate and about 200 mg/mL to about 400 mg/mL glycerin, wherein the pH of the composition is about 4 to about 8. In some embodiments, the suspension further comprises a buffering agent, a viscosity modifying agent, a vehicle, and an anti-foaming agent. In some embodiments, the suspension comprises sildenafil or a derivative thereof, glycerin, a buffering agent, a preservative, a sweetener, an antifoaming agent, a viscosity modifying agent, a flavoring agent and a vehicle.

In some embodiments, the suspensions described herein provide ready to use dosage forms. In some embodiments, the ready to use dosage forms are palatable and do not require dilution, mixing with other solvents, or further manipulation of the composition. It may be appreciated that many of the actives have been used in parenteral and solid oral medicinal products, but have not previously been used in oral liquid preparations that were stable over extended periods and that could be retrieved from the packaging in a ready to use form as contemplated herein.

In some embodiments, the suspension is room temperature stable. In some embodiments, the pharmaceutical composition requires no reconstitution. In some embodiments, the pharmaceutical compositions may not require shaking or mixing just prior to use, which is often required with suspensions.

Suspensions of insoluble drugs may also be used externally, often as protective agents. Drugs in suspension are chemically more stable than in solution. This is particularly important with certain drugs where the pharmacist is often called on to prepare such a suspension just prior to the dispensing of the preparation.

In some embodiments, the liquid pharmaceutical compositions may be in the form of a liquid dispersion, a suspension, a solution, an emulsion, a spray, a syrup, an elixir, a drop, a concentrate, or a combination thereof. In some embodiments, the pharmaceutical composition may be in the form of a dry powder to be prepared into a liquid pharmaceutical composition prior to administration to a patient.

In one of the further embodiments, the present disclosure provides liquid pharmaceutical compositions of PDE V inhibitor drugs in the form of solution dosage forms comprising PDE V inhibitor drug and one or more pharmaceutically acceptable excipients or additives selected from the group comprising of vehicles, solvents/co-solvents and/or solubilizers, pH adjusting agents and/or pH modifying agents and/or buffering agents or any combination thereof. One or more surfactants may also be added in the solution dosage forms of the present disclosure.

In one of the further embodiments, the present disclosure provides liquid pharmaceutical compositions of PDE V inhibitor drugs in the form of suspension dosage forms comprising PDE V inhibitor drug and one or more pharmaceutically acceptable excipients or additives selected from the group comprising of vehicles, solvents/co-solvents and/ or solubilizers, viscosity modifying agents, anti-foaming agents, surfactants, antioxidants, pH adjusting agents and/or pH modifying agents and/or buffering agents or any combination thereof. One or more anti-caking agents may also be added in the suspension dosage forms of the present disclosure.

Microbiological contamination presents a significant health hazard in oral liquids. Therefore, the use of preservatives become inevitable to prevent the growth of microorganisms during the product's manufacture and shelf life. Therefore, in one of the further embodiments, the liquid pharmaceutical compositions of the present disclosure may also comprise anti-microbial agents or preserving agents or preservatives.

Increase in the palatability of the drug formulations increases the patient compliance and patient acceptability towards the drug. In one of the further embodiments, the present disclosure therefore provides palatable liquid compositions comprising PDE V inhibitor drug and at least one or both selected from sweeteners/sweetening agents and flavoring agents.

The liquid compositions according to the present disclosure, without limitation include, aqueous dosage forms, alcoholic and/or hydro-alcoholic dosage forms and non-aqueous dosage forms. Aqueous dosage forms according to the present disclosure may also comprise one or more non-aqueous and/or organic solvents.

In certain embodiments, the present disclosure provides liquid pharmaceutical compositions of PDE V inhibitor drugs in the form of suspensions comprising PDE V inhibitor drug, vehicle(s), solvent(s)/co-solvent(s), solubilizer(s), viscosity modifying agent(s), preservative(s), anti-foaming agent(s), wetting agent(s), surfactant(s), pH adjusting agent(s)/pH modifier(s) or buffering agent(s) or both, sweetener(s) and flavoring agent(s).

In certain embodiments, the present disclosure provides liquid pharmaceutical compositions of PDE V inhibitor drugs in the form of solutions comprising PDE V inhibitor drug, vehicle(s), solvent(s)/co-solvent(s), solubilizer(s), preservative(s), surfactant(s), pH adjusting agent(s)/pH modifier(s) or buffering agent(s) or both, sweetener(s) and flavoring agent(s).

In some of the embodiments, the present disclosure provides the liquid pharmaceutical compositions in the form of spray which may be administered by oral route or nasal route. Sprays are known by various names such as aerosol sprays, liquid pump sprays, or activated mists etc.

In certain embodiments, the present disclosure provides liquid pharmaceutical compositions of PDE V inhibitor drugs in the form of spray comprising PDE V inhibitor drug and one or more pharmaceutically acceptable excipients selected from the group comprising of vehicles, solvents/co-solvents, solubilizers/solubilizing agents, solubility enhancing agents, penetration enhancers, mucoadhesives, stabilizing agents, buffering agents/pH adjusting agents/pH modifying agents, tonicity agents, preservatives, viscosity modifying agents, sweetening agents, flavoring agents and the like or combinations thereof.

In some of the embodiments, the liquid pharmaceutical compositions of the present disclosure are in the form of immediate release dosage forms or modified release dosage forms, such as extended release, controlled release, sustained release, prolonged release and delayed release. In some of the embodiments, the liquid pharmaceutical compositions comprise PDE V inhibitor drug and one or more suitable excipients or additives for the preparation of modified release dosage forms such as rate controlling polymers.

The liquid pharmaceutical compositions of the present disclosure may also be prepared by reconstitution of dry powder in suitable diluent or media such as water. The dry powder for reconstitution may be in the form of immediate release forms and comprise PDE V inhibitor drug and one or more suitable excipients selected form the group comprising of fillers, binders, diluents, disintegrants, pore formers, lubricants, glidants, sweeteners, stabilizing agents, antioxidants, flavoring agents, viscosity modifying agents, surfactants, preservatives and plasticizers. The dry powder for reconstitution may also be in the form of modified release forms and comprise modified release pellets, granules or particles. Such modified release pellets, granules or particles comprise one or more suitable excipients such as rate controlling polymers.

In some embodiments, the liquid pharmaceutical compositions of the invention are suitable for administration to all types of patients' population. In particular, liquid pharmaceutical compositions of the invention are suitable for pediatric and geriatric patients. The liquid pharmaceutical compositions of the invention are also useful for the patients who are unable to take solid oral therapy.

In some embodiments, the pH of the compositions of the present disclosure is between about 2.0 and about 11.0. In some of the embodiments, the pH of the compositions is between about 3.0 and about 9.0. In some of the embodiments, the pH of the compositions is between about 4.0 and about 8.0. In some of the embodiments, the pH of the compositions is between about 4.0 and about 6.0. In some of the embodiments, the pH of the compositions is between about 5.0 and about 7.0. In some of the embodiments, the pH of the compositions is between about 5.5 and about 6.5.

In one of the further embodiments, the liquid pharmaceutical compositions of the present disclosure are stable for prolonged time when stored under storage conditions. The term "storage conditions" as used herein without limitation include typical storage conditions such as 2° C.-8° C., 40° C.±2° C./75±5% RH, 30° C.±2° C./65±5% RH, 25° C.±2° C./40±5% RH, 25° C.±2° C./60±5% RH, and 40° C.±2° C./NMT 25% RH (NMT=not more than) and accelerated conditions such as 40° C.±2° C./75±5% RH. The term "prolonged time" as used herein indicates that the liquid pharmaceutical compositions of the present disclosure are stable for at least 1 month, at least 3 months, at least 6 months or at least 12 months when stored under storage conditions.

In some of the embodiments of the present disclosure, stable liquid pharmaceutical compositions or stability of the liquid pharmaceutical compositions refer to compositions which retain at least about 90%, or about least about 95%, or at least about 96%, or at least about 98%, of the labelled concentration of PDE V inhibitor drug contained in the said composition after storage under typical and/or accelerated conditions. In further embodiments, stable liquid pharmaceutical compositions or stability of the liquid pharmaceutical compositions refer to less than about 15% (area percent), or less than about 10% (area percent), or less than about 7% (area percent), or less than about 5% (area percent), or less than about 2% (area percent) of PDE V inhibitor drug-related impurities are present after storage under typical and/or accelerated conditions.

In some of the embodiments, liquid pharmaceutical compositions of the present disclosure contain no more than about 15% (area percent), or no more than about 10% (area percent), or no more than about 7% (area percent), or no more than about 5% (area percent), or no more than about 2% (area percent), or no more than about 1% (area percent), or no more than about 0.5% (area percent), or no more than about 0.2% (area percent), or no more than about 0.1% (area percent) any known or unknown single active pharmaceutical ingredient (PDE V inhibitor drug)-related impurity or other impurity after storage under typical and/or accelerated conditions.

In some of the embodiments, liquid pharmaceutical compositions of the present disclosure contain no more than about 15% (area percent), or no more than about 10% (area percent), or no more than about 7% (area percent), or no more than about 5% (area percent), or no more than about 2% (area percent), or no more than about 1% (area percent), or no more than about 0.5% (area percent), or no more than about 0.2% (area percent), or no more than about 0.1% (area percent) total active pharmaceutical ingredient (PDE V inhibitor drug)-related impurities or other impurities after storage under typical and/or accelerated conditions.

Methods for determining the stability of the liquid pharmaceutical compositions of the present disclosure with respect to a given parameter are well-known to those of skill in the art. For example, individual impurities and total impurities can be assessed by high-performance liquid chromatography (HPLC) or thin layer chromatography (TLC). Unless otherwise indicated to the contrary, a percentage amount of any individual impurities (known/unknown), or total impurities reported herein in the liquid compositions are determined by a peak area percent method using HPLC.

All percentages mentioned herein, unless otherwise indicated, are on a w/v basis, i.e. percentage ingredient (active/inactive) present in the total volume of the liquid pharmaceutical composition.

In accordance with the methods of use and administration of medicinal products, packaging materials, closures and containers vary a great deal and have to meet a wide variety of different requirements. The liquid pharmaceutical compositions of the present disclosure may be packaged within any type of pharmaceutically-acceptable package, containers, pumps, bottles with spray pump, bottles with dropper assembly, bottles, collapsible tubes, glass ampoules, stoppered vials, pre-filled syringes, low-density polyethylene (LDPE), high-density polyethylene (HDPE), polyolefin, polypropylene containers/bottles depending upon the quantity of the final dosage form. The bottles or containers without limitation include clear/transparent/opaque or amber colored glass bottles or containers and clear/transparent/opaque or amber colored plastic bottles or containers made from polyethylene, polyamide, polycarbonate, acrylic multipolymers, polypropylene, polyethylene terephthalate, polyvinyl chloride, polystyrene and the like. Depending upon the type of the containers or bottles, closures may have different shapes and sizes. The closure of the packaging material may be made from polyethylene, polyamide, polycarbonate, acrylic multipolymers, polypropylene, polyethylene terephthalate, polyvinyl chloride, polystyrene and the like.

Liquid pharmaceutical compositions of the present disclosure may be packaged in a sterile single use bottle/container that contains a unit dose for administration to a patient. Suitable bottles/containers may contain volumes between 1-10 ml, 10-20 ml, 20-40 ml, and 40-100 ml, and even more. The container may typically comprise PDE V inhibitor drug in an amount of between 10-40 mg, between 40-80 mg, between 80-130 mg, and even more. Thus, it may also be noted that the container may be a multiuse container (i.e., retains at least one more unit dose after a first unit dose is dispensed).

In some of the further embodiments, the present disclosure provides concentrate liquid compositions which may be diluted using suitable diluent before administering to the patient. In some of the embodiments, the liquid compositions of the invention are ready-to-use liquid compositions. Such ready-to-use compositions of the invention are administered directly to the patients in required doses without any prior preparation e.g. reconstitution in suitable diluent such as water.

Following embodiments of the invention describe suitable excipients which may be used to prepare liquid compositions of the present disclosure. It is in no way the intention of the present inventor(s)/applicant(s) to limit the scope of the liquid compositions of the present disclosure by the description of following embodiments. Described embodiments are for illustrative purpose only and a skilled person may use other excipients from the same or different classes as well which may provide liquid compositions of the present disclosure same or improved physico-chemical properties, palatability, stability and the like and retain or increase patients' acceptability towards the therapy. Such other excipients, classes of excipients and compositions resulted therefrom are also part of the present disclosure and covered within the scope of the present disclosure.

Vehicles may be used in the liquid compositions of the present disclosure. Vehicles are the liquid bases that carry drugs and other excipients in dissolved or dispersed state. Vehicles may be aqueous or non-aqueous or mixture thereof.

Non-aqueous solvents/cosolvents may also be added in the liquid compositions of the present disclosure to increase the solubility of poorly soluble substances and enhance the chemical stability of a drug. Suitable solvents/co-solvents, solubilizers or vehicles, that may be employed, in the liquid compositions of embodiments herein include, but are not limited to, dichloromethane, acetonitrile, ethyl acetate, acetone, propylene carbonate, water, glycerin, coconut fatty acid diethanolamide, medium and/or long chain fatty acids or glycerides, monoglycerides, diglycerides, triglycerides, structured triglycerides, soybean oil, peanut oil, corn oil, corn oil monoglycerides, corn oil diglycerides, corn oil triglycerides, polyethylene glycol, caprylocaproylmacroglycerides, caproyl 90, propylene glycol, polyoxyethylene-sorbitan fatty acid esters, polyoxyethylene castor oil derivatives, castor oil, cottonseed oil, olive oil, safflower oil, peppermint oil, coconut oil, palm seed oil, beeswax, oleic acid, methanol, ethanol, isopropyl alcohol, butanol, acetone, methyl isobutyl ketone, methyl ethyl ketone and the like or any combinations thereof.

Wetting agents as used herein are routinely used in pharmaceutical formulations, especially in liquid dosage forms to create a homogeneous dispersion of solid particles in a liquid vehicle. This process can be challenging due to a layer of adsorbed air on the particle's surface. Hence, even particles with a high density may float on the surface of the liquid until the air phase is displaced completely. The use of a wetting agent allows removal of adsorbed air and easy penetration of the liquid vehicle into pores of the particle in a short period of time. For an aqueous vehicle, alcohol, glycerin, and PG are frequently used to facilitate the removal of adsorbed air from the surface of particles. Whereas for a non-aqueous liquid vehicle, mineral oil is commonly used as a wetting agent. Non-limiting examples of wetting agents are Benzalkonium chloride, Benzethonium chloride, Cetylpyridinium chloride, Docusate sodium, Nonoxynol 9, Octoxynol, Poloxamer, Poloxamer 124, Poloxamer 188, 237, 338, 407, Polyoxyl 35 castor oil, Polyoxyl 40 hydrogenated castor oil, Polyoxyl 10 oleyl ether, Polyoxyl 20 cetylstearyl ether, Polyoxyl 40 stearate, Polysorbate 20, Polysorbate 40, Polysorbate 60, Polysorbate 80, Sodium lauryl sulfate, Sorbitan monolaurate, Sorbitan monooleate, Sorbitan monopalmitate, Sorbitan monostearate, Tyloxapol and the like or any combinations thereof.

The amount of wetting agent, e.g. glycerin, is generally about 200 mg/mL to about 400 mg/mL. In some embodiments, the wetting agent is in an amount of about 100 mg/mL to about 1000 mg/mL, about 100 mg/mL to about 800 mg/mL, about 100 mg/mL to about 600 mg/mL, about 100 mg/mL to about 500 mg/mL, about 100 mg/mL to about 400 mg/mL, about 200 mg/mL to about 1000 mg/mL, about 200 mg/mL to about 800 mg/mL, about 200 mg/mL to about 600 mg/mL, about 200 mg/mL to about 500 mg/mL, or a value between any of these ranges.

Solubility enhancing agents may include, but are not limited to, DL-methionine, caffeine, nicotinamide, vanillin, benzyl alcohol, ethanol and diethylene glycol monoethyl ether and the like or combinations thereof.

Stabilizing agents may include, but are not limited to, sodium metabisulphite, sodium bisulphite, ethylene diamine tetraacetic acid (EDTA) or salts thereof, ascorbic acid and the like or combinations thereof.

Penetration/permeation enhancers may include, but are not limited to, nicotinamide, caffeine, peppermint oil, sodium glycocholate, phospholipids, alkyl saccharides, aprotinin, benzalkonium chloride, ceramides, cetylpyridinium chloride, chitosan, chitosan-4-thiobutylamidine, cyclodextrins, dextran sulfate, dodecyl azacycloheptyl-2-ketone, ether lipids (plasmologens), glycerol, glycosylated sphingosines, lauric acid, 23-lauryl ether, lysophosphatidyl choline, menthol, methoxysalicylate, phosphatidyl choline, 1-palmitoyl-2-glutaroyl-sn-glycero-3-phosphocholine, polycarbophil cysteine, poly-L-arginine, polyoxyethylene, polyoxyethylene-9-lauryl ether, polysorbate 80, propylene glycol, EDTA, sodium deoxycholate, sodium glycocholate, sodium glycodeoxycholate, sodium lauryl sulfate, sodium salicylate, sodium taurocholate, sodium taurodeoxycholate, sodium taurodihydrofusidate, sphingolipids, sterols and the like or combinations thereof.

Mucoadhesives may also be added in the compositions of the present disclosure. Examples of suitable mucoadhesives include, but are not limited to, hydroxypropyl cellulose, gelatin, crosslinked polyacrylic acid, polymethacrylic acid, polyhydroxyethyl methacrylic acid, hydroxypropyl methyl cellulose, polyethylene glycol, sodium carboxymethyl cellulose, hyaluronic acid, chitosan, polycarbophil, pectin, xanthan gum, alginate, copolymers of dextran, polyacrylamide, acacia, copolymer of caprolactone and ethylene oxide, carbopol 934, tragacanth, eudragit and the like or combinations thereof.

The pH of an oral liquid formulation is a key point in many regards. Control of the formulation pH, could prevent large changes during storage. Therefore, most formulations utilize a buffer to control potential changes in the solution pH. The amount of buffer capacity needed is generally between 0.01 and 0.1 M, and a concentration between 0.05 and 0.5 M is usually sufficient. The selection of a suitable buffer should be based on (i) Whether the acid-base forms are listed for use in oral liquids, (ii) The stability of the drug and excipients in the buffer, and (iii) The compatibility between the buffer and container. A combination of buffers can also be used to gain a wider range of pH compared to the individual buffer alone. However, not all buffers are suitable for use in oral liquids. For example, a boric acid buffer may be used for optical and IV delivery but not in oral liquids because of its toxicity. The stabilizing effect of buffers that have multiple charged species in solution could also determine the potential reaction between excipients and API. For example, buffers that use carbonates, citrate, tartrate, and various phosphate salts may precipitate with calcium ions by forming sparingly soluble salts. However, this precipitation is dependent upon the solution pH. The activity of phosphate ions may be lowered due to interactions with other solution components.

In some embodiments, the ratio of glycerin to buffering agent is about 40:60. In some embodiments, the ratio of glycerin to buffering agent is about 50:50, about 55:45, about 65:35, about 70:30, about 75:25, about 80:20, about 90:10, about 10:90, about 20:80, about 30:70, about 35:65, about 40:60, or a range between any two of these values.

There are a number of factors that may also affect the solution pH such as temperature, ionic strength, dilution, and the amount and type of co-solvents present. For example, the pH of acetate buffers is known to increase with temperature, whereas the pH of boric acid buffers decreases with temperature. Finally, the drug in solution may itself act as a buffer. If the drug is a weak electrolyte, such as salicylic acid or ephedrine, the addition of base or acid, respectively, will create a system in which the drug can act as a buffer.

One of the most crucial factors involved in formulating a pharmaceutical suspension is the selection of an appropriate viscosity modifying agent. Viscosity modifying agents, also referred to herein as suspending agents or thickening agents, impart viscosity, and thus retard particle sedimentation. Other factors considered in the selection of the appropriate agent include desired rheological property, suspending ability in the system, chemical compatibility with other excipients, pH stability, length of time to hydrate, batch-to-batch reproducibility, and cost. Non-limiting examples of pH adjusting agents/modifiers and buffers are Acetic acid, Adipic acid, Ammonium carbonate, Ammonium hydroxide, Ammonium phosphate, Boric acid, Citric acid, Diethanolamine, Fumaric acid, Hydrochloric acid, Malic acid, Nitric acid, Propionic acid, Potassium acetate, Potassium bicarbonate, Potassium chloride, Potassium citrate, Potassium metaphosphate, Potassium phosphate, Sodium acetate, Sodium bicarbonate, Sodium borate, Sodium carbonate, Sodium chloride, Sodium citrate, Sodium glycolate, Sodium hydroxide, Sodium lactate, Sodium phosphate, Sodium proprionate, Succinic acid, Sulfuric acid, Tartaric acid, Triethylamine, Triethanolamine, Tromethamine, Trolamine and the like or any combinations thereof.

Viscosity modifying agents can be classified into cellulose derivatives, clays, natural gums, and synthetic gums. In many cases, these excipients are used in combination. There are many water soluble hydrocolloids that can act as viscosity modifying agents in the formulation of pharmaceutical suspensions. They can be of natural, semi-synthetic or synthetic origin. Non-limiting examples of viscosity modifying agents are Acacia, Agar, Alginic acid, Carbomer, Carmellose sodium, Dextrin, Gelatin, Veegum or Gel white, Gellan gum, Sodium alginate, Methylcellulose, Hydroxyethyl cellulose, Hydroxypropyl cellulose, Hydroxypropylmethyl cellulose, Hydroxypropyl starch, Hypromellose, Maltodextrin, Methylcellulose, Modified starch, Pectin, Poloxamer, Polycarbophil, Polyethylene glycol, Polyvinyl acetate, Poly (vinyl alcohol), Potassium alginate, Polyvinyl pyrrolidone, Pregelatinized starch, Propylene glycol alginate, Sodium alginate, Carboxymethyl cellulose or an alkali metal salt thereof, Microcrystalline cellulose, gum Arabic, Karaya gum, Sterculia gum, Tragacanth, Xanthan gum, Bentonite, Carageenan, Guar gum, Colloidal silicon dioxide and the like or any combinations thereof.

In some embodiments, the viscosity modifying agent is present in an amount of about 1 mg/mL to about 10 mg/mL, about 1 mg/mL to about 20 mg/mL, about 1 mg/mL to about 15 mg/mL, about 2 mg/mL to about 20 mg/mL, about 2 mg/mL to about 15 mg/mL, about 2 mg/mL to about 10 mg/mL, about 2 mg/mL to about 8 mg/mL, about 2 mg/mL to about 6 mg/mL, about 4 mg/mL to about 20 mg/mL, about 4 mg/mL to about 15 mg/mL, about 4 mg/mL to about 10 mg/mL, about 4 mg/mL to about 8 mg/mL, about 6 mg/mL to about 20 mg/mL, about 6 mg/mL to about 15 mg/mL, about 8 mg/mL to about 20 mg/mL, about 8 mg/mL to about 15 mg/mL, and any value within the foregoing range.

Although any viscosity modifying agent or agents may be used, in some embodiments, the viscosity modifying agent is xanthan gum and HPMC, which are present at about 2 to about 6 mg/mL, and about 10 mg/mL, respectively. In some embodiments, the buffering agent is citric acid monohydrate or disodium hydrogen phosphate. Additionally, some embodiments further include microcrystalline cellulose microcrystalline cellulose/sodium carboxymethylcellulose (Avicel), typically at about 20 mg/mL.

Microbiological contamination presents a significant health hazard in oral liquids. Therefore, the use of preservatives become inevitable to prevent the growth of microorganisms during the product's manufacture and shelf life, although it may be most desirable to develop a "preservative-free" formulation to address the increasing concerns about the biological activity of these compounds. Most formulations require some kind of preservative to ensure no microbial growth.

The majority of preservatives are bacteriostatic rather than bacteriocidal, and consists of both acid and nonacid types. Among the acidic types are phenol, chlorocresol, 9-phenyl phenol, alkyl esters of para-hydroxybenzoic acid, benzoic acid, boric acid, and sorbic acid, and their respective salts. Therefore, the pH of solution, and the pKa of the preservative need to be carefully evaluated prior to selecting a preservative for a formulation. Neutral preservatives include chlorobutanol, benzyl alcohol, and beta-phenylethyl alcohol. Under alkaline conditions, it is generally regarded that microbial growth is insignificant and at these pH values, the need for a preservative is not generally recommended.

Many preservatives listed in the FDA inactive ingredient guide for liquid dosage forms. Unfortunately, many of them are not recommended for use in oral liquids and hence the choice of an acceptable preservative for an oral liquid formulation is limited. In addition, the solubility of many preservatives in aqueous system may not be high enough for effective antimicrobial activity. Additionally, it is essential to understand that bacteriostatic agents like para hydroxyl benzoic acids can partition between organic and aqueous phases in a heterogenous liquid formulations in such a way that their activity is significantly reduced. Non-limiting examples of preservatives are Alcohol, Ethanol, Chlorobutanol, Phenoxyethanol, Potassium benzoate, Benzyl alcohol, Benzoic acid, Potassium sorbate, Sorbic acid, Benzalkonium chloride, Benzethonium chloride, Cetrimonium bromide, Cetylpyridinium chloride, Bronopol, Chlorbutol, Chlorocresol, Cresol, Butylparaben, Methylparaben, Propylparaben, Ethylparaben, Phenol, Thymol, Phenylethanol, Sodium benzoate, Antimicrobial solvents like Propylene glycol, Glycerin, Chloroform and the like or any combinations thereof. In addition, some formulation ingredients like nonionic surfactants, quaternary ammonium compounds, gelatin, ferric salts, calcium salts and salts of heavy metals, including silver, lead, and mercury prevent microbial growth.

Antioxidants can be compounds that can reduce a drug that has been oxidized, or compounds that are more readily oxidized than the agents they are to protect (oxygen scavengers). Many of the lipid-soluble antioxidants act as scavengers. Antioxidants can also act as chain terminators, reacting with free radicals in solution to stop the free-radical propagation cycle. Mixtures of chelating agents and antioxidants are often used because there appears to be a synergistic effect. This occurs because many of the agents act at differing steps in the oxidative process.

Some substances prone to oxidation include unsaturated oils/fats, compounds with aldehyde or phenolic groups, colors, flavors, sweeteners, plastics and rubbers, the latter being used in containers for products. Oxidation may manifest as products with an unpleasant odour, taste, appearance, precipitation, discoloration or even a slight loss of activity. The term rancidity refers to many typical off-flavors that result from autoxidation of unsaturated fatty acids that are present in oils and fats, and it affects many oils and fats. The distinct rancid odour may result from short-chain, volatile monomers resulting from the cleavage of the longer chain, less volatile oils and fats. Non-limiting examples of antioxidants are a-Tocopherol acetate, Ascorbic acid, Erythorbic acid, Butylated hydroxytoluene (BHT), d-a-Tocopherol natural, Monothioglycerol, Sodium bisulfite, Sodium sulfite, Sodium metabisulfite, Potassium metabisulfite, Acetone sodium bisulfite, Ascorbyl palmitate, Cysteine, d-a-tocopherol synthetic, Nordihydroguaiaretic acid, Sodium formaldehyde sulfoxylate, Sodium thiosulfate, Acetylcysteine, Ascorbyl palmitate, Butylated hydroxyanisole (BHA), Cysteine hydrochloride, Dithiothreitol, Propyl gallate, Thiourea and the like or any combinations thereof.

In some instances, there are insufficient drug particles in a unit dose of suspension to make a pharmaceutically elegant suspension. This is particularly true for the more highly active drugs, where the unit dose is small. Under such circumstances, the formulator will need to add more particles to improve the appearance of the final product, and also to help stabilize the suspension. To serve this purpose, bulking agents, also known as auxiliary viscosity modifying agents are used. Non-limiting examples of bulking agents are Calcium carbonate, Calcium hydroxide, Cellulose, Crospovidone, Dibasic calcium phosphate, Magnesium carbonate, Magnesium hydroxide, Microcrystalline cellulose, Silica (silicon dioxide), Titanium dioxide and the like or any combinations thereof.

Many different materials are capable of adsorbing onto the suspended particles, e.g. natural gums, cellulosics and non-ionic surfactants. However, not all of them are able to act as protective colloids and provide steric hindrance to caking at a sufficiently low concentration. High levels of surfactants, for example, can increase gastro-intestinal motility. Higher molecular weight gums and cellulosics may also cause an unacceptable increase in the viscosity of the system. There are, however, certain polymers, or grades of polymers, that are capable of acting as protective colloids at concentrations that do not markedly increase the viscosity of the system, or increase gut motility, etc. Such materials include poloxamers, lower molecular weight grades of povidone, and low molecular weight grades of some other hydrophilic colloids.

Surfactant is a general name for materials that possess surface activity; in solution they tend to orient at the surface of the liquid. There are several general classes of surfactants: anionic, cationic, amphoteric and non-ionic. Surfactants are amphiphilic molecules, i.e. part of the molecule is hydrophilic, and part is lipophilic. This combination of the two opposite affinities in the same molecule causes them to orient to the interface and thereby reduce the interfacial tension between the continuous and disperse phases, such as in emulsions and suspensions. Ionic surfactants work primarily through electrostatic forces, whereas non-ionic surfactants work primarily through steric forces. Non-limiting examples of surfactants are Sodium lauryl sulfate, Docusate sodium, Cocamidopropyl amino betaine, Polyoxyethylene sorbitan fatty acid esters (Polysorbate, Tween®), Polyoxyethylene 15 hydroxystearate (Macrogol 15 hydroxystearate, Solutol HS15®), Polyoxyethylene castor oil derivatives (Cremophor® EL, ELP, RH 40), Polyoxyethylene stearates (Myrj®), Sorbitan fatty acid esters (Span®), Polyoxyethylene alkyl ethers (Brij®), Polyoxyethylene nonylphenol ether (Nonoxynol®) and the like or any combinations thereof. Anti-foaming agents may be used in the preparation of the liquid pharmaceutical compositions of the present disclosure to lower the surface tension and cohesive binding of liquid phase. Non-limiting examples of anti-foaming agents are simethicone, organic phosphates, alcohols, paraffin oils, stearates, glycols and the like or any combinations thereof. In some embodiments, the anti-foaming agent is 30% simethicone emulsion.

Chelating agents, also known as sequestrants, are molecules that have the ability to form stable complexes with metal ions, particularly di-valent and tri-valent metal ions including trace metals and heavy metals. These metal ions are often implicated in API degradation by acting as catalysts, e.g. Mg$^{2+}$ will catalyze both ester hydrolysis and the Maillard interaction between primary or secondary amines and reducing sugars. Oxidative degradation is also often catalyzed by heavy metals. In addition, certain trace metals are required for microbial growth, and chelation (sequestration) to form complexes can help prevent microbial growth and spoilage, and thus allow lower levels of microbicidal agents to be used. Non-limiting examples of chelating agents are Calcium disodium edetate, Disodium edetate, Edetic acid (also known as ethylenediaminetetraacetic acid/ EDTA), Citric acid and the like or any combinations thereof.

Palatability of oral medicines is an important factor in compliance. There are several components to palatability including flavor, mouth-feel and sweetness. Most patients prefer medicines that are not too bitter but may be slightly "tart" (acidic). Most APIs are bitter. However, for bitterness to develop, the drug must be sufficiently soluble to interact with taste receptors on the tongue. For insoluble APIs in the form of suspensions, components of the suspension are also bitter, e.g. preservatives, or very salty, e.g. buffer systems. However, a slight saltiness and a slight bitterness are desirable for palatability.

Traditionally, oral medicines were sweetened using Syrup (concentrated sucrose solution) or honey (contains fructose). However, these materials are inadequate for the formulation of many products because they simply are not able to adequately mask the very bitter taste of many pharmaceutical materials, including APIs and excipients. Several alternative sweetening agents have been developed over the years to better mask unpleasant tastes in both processed foods and pharmaceuticals.

Several of the materials classified as sweetening agents are sugar alcohols (also known as polyhydric alcohols, polyols and hydrogenated sugars). Several of the commonly used sweetening agents are ionic and have the potential to interact with other components of the suspension. Some sweetening agents are more stable than others in aqueous solution. These will be important factors in the final selection of the sweetening agent. Non-limiting examples of sweetening agents are Glucose, Sucralose, Trehalose, Fructose, Xylose, Dextrose, Galactose, Tagatose, Maltose, Sucrose, Glycerol, Dulcitol, Mannitol, Lactitol, Sorbitol, Xylitol, Saccharine or the corresponding sodium, potassium or calcium salt, Cyclamate or the corresponding sodium or calcium salt, Aspartame, or Acesulfame or the potassium salt thereof, Dulcin or Ammonium glycyrrhizinate, Alitame, Inulin, Isomalt, Neohesperidin dihydrochalcone, Thaumatin and the like or any combinations thereof.

Flavors are used to improve the palatability of oral medicines. One problem that can arise with oral suspensions is that the suspension may produce a "cloying" sensation in the mouth. While this is not the same as a bitter taste, it can nevertheless cause problems for the patient and affect compliance. This can be a particular problem with high levels of inorganic components. Flavors can help reduce this "cloying" taste and thereby improve palatability, and ultimately patient compliance.

There are many different flavors, and most flavors are complex mixtures of many components. Today most flavors are developed by specialist flavor houses, and typically the flavor is formulated for each individual application. Since flavor will be part of the suspension continuous phase, it has the maximum potential for interaction, and some flavor components may cause stability issues (physical or chemical) for the suspension. Flavor development and compounding is a specialist discipline. When deciding on which particular flavor is appropriate, the flavor specialist would benefit from knowledge of the other likely components in the suspension, just as the formulation scientist would benefit from knowledge of the components of the flavor. Flavors can adsorb onto finely divided solids, thus reducing their effectiveness. They can also be absorbed by packaging/ Flavor preferences vary with age, but the citrus flavors appear generally acceptable to most age groups. Non-limiting examples of flavoring agents are synthetic flavor oils and flavoring aromatics and/or natural oils, extracts from plants leaves, flowers, fruits, and so forth and the like or any combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil and the like or any combinations thereof. Also useful as flavors are vanilla, citrus oil, including lemon, orange, grape, lime and grapefruit, and fruit essences, including apple, banana, pear, peach, strawberry, raspberry, cherry, plum, pineapple, apricot, and so forth and the like or any combinations thereof. Solid forms, such as spray dried forms of flavoring agents, may also be useful in the liquid compositions disclosed herein.

Coloring agents may also be used in the preparation of the liquid compositions of the present disclosure. Pharmaceutical colors come in two types; soluble dyes and insoluble pigments. For pharmaceutical suspensions intended for oral use, soluble dyes are often used; however, pigments may also be used and would be part of the disperse phase. Soluble dyes have the potential to interact with other components of the formulation.

In some embodiments, the liquid pharmaceutical compositions of the present disclosure are non-caking liquid compositions. The term "non-caking" as used herein means that the liquid composition has a smooth consistency and doesn't contain any caking or clumping particles, by visual inspection. Also, the liquid composition in accordance with the present disclosure does not cake or clump during manufacture, i.e., when mixed with excipients. Nor does it cake or clump upon storage, even under relatively humid conditions, e.g., a relative humidity of about 75% or greater and when stored for relatively long periods such as about 6 months or longer and even at elevated temperatures of about 40° C. or greater, or at any combination of such humidity, time and temperature parameters. Thus, the liquid compositions in accordance with the present disclosure will remain non-caking during typical storage and use conditions.

In some embodiments, the PDE V inhibitor may be selected from the group consisting of Avanafil, AWD-12-250, BF/GP-385, BMS-22313, BMS-341400, CP-248, CP-461, DA-8 159, Dasantafil, DMPPO, E-4021, E-8010, EMD-82639, EMR-62203, Exisulind, FR-181074, FR-226807, FR-229934, GF-248, KF-31327, KT-734, LAS-34 179, Lusupultide, MJ-12504, NCX-91 1, NM-702, OPC-35564, OSI-461, QAD-171A, Roflumilast, SB-9623 1, SCH-46642, SCH-51866, SCH-59498, Sildenafil, Sildenafil citrate, SK-350, SK-3530, SKF-96231, Sophoflavescenol, SR-265579, T-0156, T-1032, Tadalafil, UK-1 14502, UK-1 14542, UK-357903, UK-369003, UK-371800, UK-83405, Vardenafil, WIN-65579, WS-63967, YC-1 and Zaprinast, a derivative thereof, and any combination thereof.

In one of the further embodiments, the liquid pharmaceutical compositions of the present disclosure comprise particles of PDE V inhibitor or a derivative thereof, wherein the d90 of the particles is less than about 1000 microns, or less than about 950 microns, or less than about 900 microns, or less than about 850 microns, or less than about 800 microns, or less than about 750 microns, or less than about 700 microns, or less than about 650 microns, or less than about 600 microns, or less than about 550 microns, or less or less than about 200 microns, or less than about 150 microns, or less than about 100 microns, or less than about 90 microns or less than about than about 500 microns, or less than about 450 microns, or less than about 400 microns, or less than about 350 microns, or less than about 300 microns, or less than about 250 microns, or less than about 200 microns, or less than about 150 microns, or less than about 100 microns, or less than about 90 microns, or less than about 80 microns, or less than about 70 microns, or less than about 60 microns, or less than about 50 microns, or less than about 40 microns, or less than about 30 microns, or less than about 20 microns, or less than about 10 microns, or less than about 5 microns, or less than about 2 microns, or less than about 1 microns, or less than about 0.5 pm.

In one of the further embodiments, the liquid pharmaceutical compositions of the present disclosure comprise particles of PDE V inhibitor or a derivative thereof, wherein the d90 of the particles is less than about 1000 microns, or less than about 950 microns, or less than about 900 microns, or less than about 850 microns, or less than about 800 microns, or less than about 750 microns, or less than about 700 microns, or less than about 650 microns, or less than about 600 microns, or less than about 550 microns, or less than about 500 microns, or less than about 450 microns, or less than about 400 microns, or less than about 350 microns, or less than about 300 microns, or less than about 250 microns, microns, about 90 microns, about 80 microns, about 70 microns, about 60 microns, about 50 microns, or less than about 40 microns, or less than about 30 microns, or less than about 20 microns, or less than about 10 microns, or less than about 5 microns, or less than about 2 microns, or less than about 1 microns, or less than about 0.5 microns.

In some embodiments, the d90 of the PDE V particles is about 1000 microns, about 950 microns, about 900 microns, about 850 microns, about 800 microns, about 750 microns, about 700 microns, about 650 microns, about 600 microns, about 550 microns, about 500 microns, about 450 microns, about 400 microns, about 350 microns, about 300 microns, about 250 microns, about 200 microns, about 150 microns, about 100 microns, about 90 microns, about 80 microns, about 70 microns, about 60 microns, about 50 microns, about 40 microns, about 30 microns, about 20 microns, about 10 microns, about 5 microns, about 2 microns, about 1 microns, about 0.5 microns, or a range of any two of these values (e.g. about 5 microns to about 200 microns, about 1 micron to about 1000 microns, about 1 micron to about 500 microns, about 1 micron to about 200 microns, about 5 microns to about 1000 microns, or the like).

In some embodiments, a pharmaceutical composition for oral delivery comprises a PDE V inhibitor, and a wetting agent. In some embodiments, a pharmaceutical composition for oral delivery comprises a PDE V inhibitor, and a wetting agent, wherein the pH of the composition is about 4.0 to about 8.0. In some embodiments, a pharmaceutical composition for oral delivery comprises a PDE V inhibitor, a buffering agent, and a wetting agent. In some embodiments, a pharmaceutical composition in the form of a suspension for oral delivery comprises a PDE V inhibitor, a viscosity modifying agent, a buffering agent, and glycerin. In some embodiments, a pharmaceutical composition in the form of a suspension for oral delivery comprises a PDE V inhibitor, a viscosity modifying agent, a buffering agent in an amount sufficient to make the composition pH about 4 to about 8; and about 200 mg/mL to about 400 mg/mL glycerin.

Methods of Preparation

In one of the embodiments, general formula of the liquid pharmaceutical compositions according to the present disclosure may be provided as follows.

TABLE 1

General formula of liquid pharmaceutical compositions of the present disclosure

| | | Quantity (% w/v) | |
|---|---|---|---|
| Sr No. | Ingredient | Solution dosage form | Suspension dosage form |
| 1 | Active pharmaceutical ingredient (PDE V inhibitor drug) | 0.01-25 | 0.01-25 |
| 2 | viscosity modifying agent(s) | — | 0.01-10 |
| 3 | Preservative(s) | 0.01-10 | 0.01-10 |
| 4 | Wetting agent(s) | — | 0-90 |
| 5 | pH adjusting agent(s)/pH modifying agents | Q.S. to adjust the pH | Q.S. to adjust the pH |
| 6 | Buffering agent(s) | Q.S. to adjust the pH | Q.S. to adjust the pH |
| 7 | Solvent(s)/co-solvent(s) | Q.S. | Q.S. |
| 8 | Solubilizer(s) | Q.S. | Q.S. |
| 9 | Anti-foaming agent(s) | — | 0.01-10 |
| 10 | Anti-caking agent(s) | — | 0-10 |
| 11 | Antioxidant | — | 0-10 |
| 12 | Surfactant(s) | 0-10 | 0.01-10 |
| 13 | Sweetening agent(s) | 0.01-5 | 0.01-5 |
| 14 | Flavoring agent(s) | 0.01-5 | 0.01-5 |
| 15 | Coloring agent(s) | 0-2 | 0-2 |
| 16 | Vehicle(s) | QS. | Q.S. |

Q.S. = Quantity Sufficient

Those who are skilled in the art will appreciate that different types of liquid pharmaceutical compositions as described herein can be prepared by using suitable excipients or additives known in the art. Thus, the name of excipients or additives and proportionate range thereof provided in the Table 1 is provided herein for the illustration purpose only and should not be construed as the exact or the only scope of the present disclosure. The liquid pharmaceutical compositions of the present disclosure may be prepared using suitable excipients or additives in any suitable amount.

In one of the further embodiments, the present disclosure provides processes for the preparation of the liquid pharmaceutical compositions of PDE V inhibitor drugs.

Process-1: Preparation of Solution Dosage Forms
1. Add one or more sweetener(s) followed by one or more preservative(s) in the suitable vehicle;
2. Add PDE V inhibitor drug or salt thereof;
3. Add one or more buffering agent(s) to adjust the desired pH followed by flavoring agent; and
4. Adjust the volume to the required quantity with vehicle.

Process-2: Preparation of Solution Dosage Forms
1. Add one or more solvent(s) followed by one or more sweetener(s) and one or more. preservative(s) in the suitable vehicle;
2. Add PDE V inhibitor drug or salt thereof;
3. Add one or more buffering agent(s) to adjust the desired pH followed by flavoring agent; and
4. Adjust the volume to the required quantity with vehicle.

Process-3: Preparation of Suspension Dosage Forms
1. Add one or more preservative(s) followed by one or more buffering agent(s) to adjust the desired pH in the suitable vehicle;
2. Add one or more sweetener(s) and flavoring agent followed by one or more suitable solvent(s)/co-solvent(s) and/or one or more solubilizer(s);
3. Add one or more viscosity modifying agent(s) followed by one or more anti-foaming agent(s) and one or more surfactant(s);

4. Add PDE V inhibitor drug or salt thereof, and
5. Adjust the volume to the required quantity with vehicle.

Process-4: Preparation of Suspension Dosage Forms
1. Add and mix one or more solubilizer(s) in the suitable vehicle;
2. Add one or more viscosity modifying agent(s);
3. Add one or more antioxidant(s) and one or more sweetener(s) dissolved in the suitable solvent(s) to step (2);
4. Add PDE V inhibitor drug or salt thereof, and
5. Add flavoring agent and adjust the volume to the required quantity with vehicle.

Process-5: Preparation of Suspension/Solution Dosage Forms
1. One or more preservatives are added in the sufficient quantity of the vehicle;
2. One or more sweetener, optionally one or more antifoaming agents, optionally one or more surfactants, one or more solvents/co-solvents or solubilizers are sequentially added;
3. PDE V inhibitor drug or salt thereof is added;
4. Optionally one or more viscosity modifying agents, one or more pH adjusting agents and/or pH modifying agents and/or buffering agents (to adjust the pH), optionally one or more solvents/cosolvents and one or more flavoring agents are added sequentially; and
5. Required quantity of vehicle is added to make up the volume to the final quantity.

Process-6: Preparation of Suspension Dosage Forms
1. Mix suitable solubilizing agent and solvent;
2. Add PDE V inhibitor drug or salt or derivative thereof;
3. Add sufficient quantity of vehicle followed by addition of flavoring agent; and
4. Adjust the volume to the required quantity with vehicle.

Process-7: Preparation of Solution/Suspension Dosage Forms
1. One or more preservative(s) are added in suitable vehicle;
2. Optionally one or more buffering agent(s) are added;
3. Optionally one or more surfactant(s) are added;
4. PDE V inhibitor drug or salt or derivative thereof is added;
5. Optionally one or more solvent(s) are added;
6. Optionally one or more viscosity modifying agent(s) are added;
7. One or more sweeteners are added followed by addition of flavoring agent;
8. Adjust the volume to the required quantity with vehicle.

Process-8: Preparation of Suspension Dosage Form
1. Take vehicle(s), buffering agent(s) and preservative(s) one by one and mix till get dissolved;
2. Add and mix sweetener(s) and antifoaming agent(s) one by one in the mixture of step (1) till it gets uniformly dispersed;
3. Add and mix solvent(s)/co-solvent(s) in the mixture of step (2) till it gets uniformly dispersed;
4. Add and mix PDE V inhibitor in the mixture of step (3) till it gets uniformly dispersed;
5. Add and mix viscosity modifying agent(s) in the mixture of step (4) till it gets uniformly dispersed;
6. Finally add flavouring agent(s) in the mixture of step (5) and make up the desired volume using vehicle(s) and mix till uniform suspension is formed.

Process-9: Preparation of Suspension Dosage Form
1. Take vehicle(s), buffering agent(s) and preservative(s) one by one and mix till get dissolved;
2. Add and mix sweetener(s) as well as antifoaming agent(s) one by one in the mixture of step (1) till it gets uniformly dispersed;
3. Add and mix solvent(s)/co-solvent(s) and surfactant(s) one by one in the mixture of step (2) till it gets uniformly dispersed;
4. Add and mix PDE V inhibitor in the mixture of step (3) till it gets uniformly dispersed;
5. Add and mix viscosity modifying agent(s) in the mixture of step (4) till it gets uniformly dispersed;
6. Finally add flavouring agent(s) in the mixture of step (5) and make up the desired volume using vehicle(s) and mix till uniform suspension is formed.

Those who are skilled in the art can understand that some variations in the process described herein can be adopted. A skilled person may omit use of some pharmaceutical excipients as described herein above. A skilled person may also alternatively use some or all pharmaceutical excipients as described herein from the same excipient classes. Such variations are well within the scope of the present disclosure. A skilled person can also change and/or omit steps of their sequences of the herein described process for the purposes of suitability and convenience where one or more pharmaceutically acceptable excipients may or may not be used without affecting and diminishing the quality and characteristics of the resulting product. Such variations/changes/omissions/additions are well within the scope of the present disclosure.

The liquid pharmaceutical compositions of the present disclosure may also be prepared using processes generally known to those skilled in the art. The processes for the preparation of liquid pharmaceutical compositions of the present disclosure may vary depending upon the final dosage form, e.g. solution, suspension, etc. The processes for the preparation of the liquid compositions of the present disclosure may comprise multiple steps. Such steps may include sequential addition of suitable excipients/additives. Such steps may also include physical processes for example mixing, stirring, agitation etc.

In one of the embodiments, the present disclosure provides a liquid composition comprising Sildenafil or its pharmaceutically acceptable salts and chemical derivatives such as polymorphs, solvates, hydrates, anhydrous forms, prodrugs, chelates, and complexes thereof and one or more pharmaceutically acceptable excipients selected from the group comprising of vehicles, solvents or co-solvents or solubilizers, viscosity modifying agents or thickening agents or viscosity modifying agents, anti-foaming agents, stabilizing agents, anti-oxidants, pH adjusting agents or pH modifying agents or buffering agents, wetting agents, bulking agents or auxiliary viscosity modifying agents, chelating agents, surfactants, preservatives, sweetening agents, coloring agents, flavoring agents or combinations thereof.

In one of the embodiments, the present disclosure provides a liquid composition comprising Tadalafil or its pharmaceutically acceptable salts and chemical derivatives such as polymorphs, solvates, hydrates, anhydrous forms, prodrugs, chelates, and complexes thereof and one or more pharmaceutically acceptable excipients selected from the group comprising of vehicles, solvents or co-solvents or solubilizers, viscosity modifying agents or thickening agents or viscosity modifying agents, anti-foaming agents, stabilizing agents, anti-oxidants, pH adjusting agents or pH modifying agents or buffering agents, wetting agents, bulking agents or auxiliary suspending agents, chelating agents, surfactants, preservatives, sweetening agents, coloring agents, flavoring agents or combinations thereof.

Methods of Treatment

In one of the embodiments, the liquid pharmaceutical compositions of the present disclosure are suitable for administration to a subject to treat or prevent a disease or a condition. Preferably, the subject is a mammal. More preferably, the mammal is a human. Preferably, the disease or condition is a disease or condition that is treatable by the administration of PDE V inhibitor drug as described herein.

In one of the embodiments, the present disclosure is directed to the method for the treatment of a disease or a condition that can be treated by PDE V inhibitor drugs comprising administering to a patient, such as human, an effective dosage amount of a liquid pharmaceutical composition comprising PDE V inhibitor drug and one or more pharmaceutically acceptable excipients or additives as disclosed and described herein. In one of the further embodiments, the present disclosure is directed to the method for the treatment of at least one disease or condition selected from the group comprising of hypertension, pulmonary hypertension, arterial hypertension, pulmonary arterial hypertension, erectile dysfunction, cirrhosis, solid tumor, heart failure, cerebral vasospasm, arthritis, rheumatoid arthritis, atherosclerosis, congenital heart diseases, Parkinson's disease, neonatal encephalopathy, pre-eclampsia, prostate cancer, pancreatic cancer, hepatic encephalopathy, aortic stenosis, cystic fibrosis, peripheral arterial occlusive disease, sickle cell disease, priapism, age-related macular degeneration, schizophrenia, bronchopulmonary dysplasia, impotence, lymphangioma, dysmenorrhea, urinary incontinence, chronic obstructive pulmonary disease, lymphatic malformations, Duchenne muscular dystrophy, Becker muscular dystrophy, pulmonary fibrosis, nontuberculous mycobacterial infection, idiopathic pulmonary fibrosis, Raynaud's phenomenon, prostatic hyperplasia, benign prostatic hyperplasia Waldenstrom's macroglobulinemia and the like comprising administering to a patient, such as human, an effective dosage amount of a liquid pharmaceutical composition comprising PDE V inhibitor drug and one or more pharmaceutically acceptable excipients or additives as disclosed and described herein.

In one of the further embodiments, the present disclosure is directed to use liquid pharmaceutical compositions of the present disclosure for the treatment of a disease or a condition that can be treated by administration of PDE V inhibitor drugs. In one of the further embodiments, the present disclosure is directed to use liquid pharmaceutical compositions of the present disclosure for the treatment of at least one disease or a condition selected from the group comprising of hypertension, pulmonary hypertension, arterial hypertension, pulmonary arterial hypertension, erectile dysfunction, cirrhosis, solid tumor, heart failure, cerebral vasospasm, arthritis, rheumatoid arthritis, atherosclerosis, congenital heart diseases, Parkinson's disease, neonatal encephalopathy, pre-eclampsia, prostate cancer, pancreatic cancer, hepatic encephalopathy, aortic stenosis, cystic fibrosis, peripheral arterial occlusive disease, sickle cell disease, priapism, age-related macular degeneration, schizophrenia, bronchopulmonary dysplasia, impotence, lymphangioma, dysmenorrhea, urinary incontinence, chronic obstructive pulmonary disease, lymphatic malformations, Duchenne muscular dystrophy, Becker muscular dystrophy, pulmonary fibrosis, nontuberculous mycobacterial infection, idiopathic pulmonary fibrosis, Raynaud's phenomenon, prostatic hyperplasia, benign prostatic hyperplasia Waldenstrom's macroglobulinemia and the like.

The liquid pharmaceutical compositions of the present disclosure are proposed to have unexpectedly dramatic dissolution profiles. Rapid dissolution of an administered active agent is preferable, as faster dissolution generally leads to greater bioavailability and faster onset of action. To improve the dissolution profile and bioavailability of PDE V inhibitor drug it would be useful to increase dissolution of the PDE V inhibitor drug used so that it could attain a level close to 100% dissolution of the drug substance.

The liquid pharmaceutical compositions of the present disclosure comprising PDE V inhibitor drug or salt thereof or derivative thereof, exhibit improved or comparable pharmacokinetic profiles as compared to marketed or known compositions. For example, the Cmax and/or AUC of the liquid pharmaceutical compositions of PDE V inhibitor drug of the present disclosure can be greater than or substantially equal to the Cmax and/or AUC for known or marketed compositions administered at the same dose. In addition, the Tmax of the liquid compositions of the present disclosure can be lower than or substantially equal to that obtained for a known or marketed compositions, administered at the same dose. In addition, combinations of an improved or comparable Cmax, AUC and Tmax profile can be exhibited by the liquid compositions of the invention, as compared to known or marketed compositions. In further embodiments, the liquid compositions of the present disclosure may result in minimal different absorption levels when administered under fed as compared to fasting conditions.

In one of the embodiments, the liquid compositions of the present disclosure exhibit in comparative pharmacokinetic testing with marketed or known formulation, administered at the same dose, a Tmax not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the Tmax exhibited by the marketed or known formulation.

In one of the further embodiments, the liquid compositions of the present disclosure exhibit in comparative pharmacokinetic testing with marketed or known formulation, administered at the same dose, a Cmax which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the Cmax exhibited by the marketed or known formulation.

In one of the further embodiments, the liquid compositions of the present disclosure exhibit in comparative pharmacokinetic testing with marketed or known formulation, administered at the same dose, an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the marketed or known formulation.

In one of the further embodiments, the Tmax of PDE V inhibitor drug or salt thereof used for the preparation of the liquid composition according to the present disclosure, when assayed in the plasma of the mammalian subject, is less than about 6 to about 8 hours. In other embodiments of the invention, the Tmax of PDE V inhibitor drug or salt thereof is less than about 6 hours, less than about 5 hours, less than about 4 hours, less than about 3 hours, less than about 2 hours, less than about 1 hour, or less than about 30 minutes after administration.

In some embodiments, the liquid compositions of the present disclosure exhibit improved or comparable bioavailability as compared to known or marketed compositions.

Example 1

An exemplary formulation for sildenafil/sildenafil citrate made in accordance with the embodiments described herein is as follows:

TABLE 2

Sildenafil oral suspension

| Sr. No. | Ingredients | Role of Ingredients | Prototype Formula % w/v | (mg/mL) |
|---|---|---|---|---|
| 1 | Sildenafil | Active | 1 | 10 |
| 2 | sodium benzoate | Preservative | 0.2 | 2 |
| 3 | Glycerin | Wetting agent | 40 | 400 |
| 4 | Sucralose Powder | Sweetener | 0.5 | 5 |
| 5 | 30% Simethicone Emulsion | Antifoaming | 0.05 | 0.5 |
| 6 | Citric acid monohydrate | Buffering agent | 0.28 | 2.8 |
| 7 | Xanthan gum | Viscosity | 0.25 | 2.5 |
| 8 | Tri-sodium citrate dihydrate | Buffering agent | 0.486 | 4.8 |
| 9 | Acesulfame K | Sweetener | 0.1 | 1 |
| 10 | Strawberry Flavor | Flavor | 0.01 | 0.1 |
| 11 | Water | Vehicle | q.s to 100 ml | q.s to 1 ml |

Example 2

An exemplary formulation for tadalafil made in accordance with the embodiments described herein is as follows:

TABLE 3

Tadalafil oral suspension

| Sr. No. | Ingredients | Role of Ingredients | Prototype Formula % w/v | (mg/mL) |
|---|---|---|---|---|
| 1 | Tadalafil | Active | 0.4 | 4 |
| 2 | sodium benzoate | Preservative | 0.24 | 2.4 |
| 3 | Glycerin | Wetting agent | 40 | 400 |
| 4 | Sucralose Powder | Sweetener | 0.1 | 1 |
| 5 | 30% Simethicone Emulsion | Antifoaming | 0.05 | 0.5 |
| 6 | Citric acid monohydrate | Buffering agent | 0.28 | 2.8 |
| 7 | Xanthan gum | Viscosity | 0.25 | 2.5 |
| 8 | Tri-sodium citrate dihydrate | Buffering agent | 0.486 | 4.8 |
| 9 | Polysorbate80 | Wetting agent | 0.1 | 1 |
| 10 | Frozen peppermint flavor | Flavour | 0.01 | 0.1 |
| 11 | Water | vehicle | q.s to 100 ml | q.s to 1 ml |

0.1% active may also be used with the remaining excipients are at the same concentration in both strengths Example 3

Stability testing was performed on the sildenafil suspension of Example 1 as outlined in the tables below. The suspension was found to be stable.

TABLE 4

Stability of Sildenafil formulation

| Test parameters | Specification (shelf life) | INITIAL | 40° C./75% 3M | 40° C./75% 6M | 25° C./60% 3M | 25° C./60% 6M |
|---|---|---|---|---|---|---|
| Description | White to off white suspension | White to off white suspension | White to off white suspension | White to off white suspension | White to off white suspension | White to off white suspension |
| Assay of Sildenafil citrate | 95-105% | 99.40% | 100% | 102.80% | 98.6% | 98.90% |
| Assay of Sodium Benzoate | 80-110% | 98.10% | 97.6% | 100.00% | 98.4% | 98.90% |
| pH | 3.5-5.5 | 4.66 | 4.76 | 4.62 | 4.74 | 4.6 |
| Related Substances Sildenafil Isobutyl analogue [Ph. Eur. Impurity A] | Not more than 0.5% | ND | ND | ND | ND | ND |
| Sildenafil N-oxide [Ph. Eur. Impurity-B] | Not more than 0.30% | 0.02% | 0.03% | 0.01% | 0.04% | 0.01% |
| Single maximum unknown impurity | Not more than 0.2% | 0.02% | 0.03% | 0.02% | 0.04% | 0.02% |
| Total impurities | Not more than 1.0% | 0.00% | 0.06% | 0.07% | 0.07% | 0.06% |

Example 4

Stability testing was performed on the tadalafil suspension of Example 2 as outlined in the tables below. The suspension was found to be stable.

TABLE 5

Stability of Tadalafil Formulation

| | Test parameters | | |
|---|---|---|---|
| | INITIAL | 40° C./25% 6M | 25° C./60% 6M |
| | Description | | |
| | Off white suspension | Off white suspension | Off white suspension |
| Assay of Tadalafil | 101.7% | 102.3% | 101.0% |
| Assay of Sodium Benzoate | 99.60% | 102.3% | 101.3% |
| pH | 4.83 | 5.0 | 5 |
| Related substances by HPLC | | | |
| Unspecified Impurities | ND | 0.01 | ND |
| Total impurities | ND | 0.02 | ND |

Example 5

A comparison of the dissolution profile of sildenafil formulation having various particle sizes (d90) was performed.

TABLE 6

Sildenafil particle size comparison

| Test parameters | Specification | Marketed product | SILL1012 | SILL1028 |
|---|---|---|---|---|
| Description | White to off white suspension | White suspension | White suspension | White suspension |
| Description | White to off white suspension | White suspension | White suspension | White suspension |
| Assay of Sildenafil citrate | 95-105% | 100.20% | 96.90% | 101.30% |
| Particle size distribution (Micron) | d(0.1) | 0.8 | 4 | 1.6 |
| | d(0.5) | 5.6 | 19 | 6.7 |
| | d(0.9) | 16.3 | 127 | 16.4 |
| Dissolution (Mcilvaine buffer pH 5.0) | 10 Min | 85.10% | 29.50% | 77.40% |
| | 15 Min | 93.10% | 42.90% | 88.30% |
| | 20 Min | 96.50% | 73.80% | 91.40% |
| | 30 Min | 100.30% | 89.70% | 93.40% |
| | 45 Min | 101.20% | 96.00% | 93.60% |

Example 6

A comparison of the dissolution profile of tadalafil formulation having various particle sizes (d90) was performed.

TABLE 7

Tadalafil particle size comparison

| Test parameters | Specification | Marketed product Initial | TIDL3008 Initial | TIDL3010 Initial |
|---|---|---|---|---|
| Description | White to off white suspension | Orange, film coated, almond shaped tablet | Off white suspension | Off white suspension |
| Assay of Tadalafil | 95-105% | 100.10% | NP | 98.40% |
| Particle size distribution (Micron) | d(0.1) | NA | 9 | 1 |
| | d(0.5) | NA | 29 | 3 |
| | d(0.9) | NA | 82 | 8 |
| Dissolution (0.5% Sodium lauryl sulfate) | 10 Min | 85.90% | 36.00% | 94.50% |
| | 15 Min | 95.90% | 42.00% | 95.40% |
| | 30 Min' | 99.10% | 47.20% | 96.70% |

It should be understood that various changes and modifications to the embodiments described herein will be apparent to those skilled in the art. Such changes and modifications can be made without departing from the spirit and scope of the subject matter of the present disclosure and without diminishing its intended advantages. It is therefore intended that such changes and modifications be covered within the scope of the present disclosure.

The invention claimed is:

1. A liquid oral pharmaceutical composition comprising about 4 mg/mL tadalafil or a pharmaceutically acceptable salt thereof;
a pharmaceutically acceptable excipient comprising a wetting agent comprising ethanol, glycerin, propylene glycol, or a combination thereof in an amount of about 100 mg/mL to about 1000 mg/mL; and
a vehicle comprising water;
wherein the pharmaceutical composition has a pH of from about 4 to about 8;
wherein the pharmaceutically acceptable excipient further comprises a preservative, a sweetener, a flavorant, or a combination thereof; and
wherein the preservative is present in an amount of from about 0.1 mg/mL to about 100 mg/mL, the sweetener is present in an amount of: from about 0.1 mg/mL to about 50 mg/mL, and the flavorant is present in an amount of from about 0.1 mg/mL to about 50 mg/mL.

2. The liquid oral pharmaceutical composition of claim 1, wherein the tadalafil comprises particulate tadalafil having a d90 particulate size of from about 1 micron to about 200 microns.

3. The liquid oral pharmaceutical composition of claim 1, wherein the tadalafil comprises particulate tadalafil having a d90 particulate size of from about 1 micron to about 100 microns.

4. The liquid oral pharmaceutical composition of claim 1, wherein the tadalafil comprises particulate tadalafil having a d90 particulate size of from about 5 microns to about 10 microns.

5. The liquid oral pharmaceutical composition of claim 1, wherein the liquid oral pharmaceutical composition has a pH of from about 4 to about 6.

6. The liquid oral pharmaceutical composition of claim 1, wherein the liquid oral pharmaceutical composition has a pH of about 5.

7. The liquid oral pharmaceutical composition of claim 1, wherein the wetting agent is present in an amount of from about 100 mg/mL to about 900 mg/mL.

8. The liquid oral pharmaceutical composition of claim 1, wherein the wetting agent is present in an amount of from about 100 mg/mL to about 800 mg/mL.

9. The liquid oral pharmaceutical composition of claim 1, wherein the wetting agent is present in an amount of from about 100 mg/mL to about 700 mg/mL.

10. The liquid oral pharmaceutical composition of claim 1, wherein the wetting agent is present in an amount of from about 200 mg/mL to about 600 mg/mL.

11. The liquid oral pharmaceutical composition of claim 1, wherein the pharmaceutically acceptable excipient further comprises a viscosity modifying agent comprising an acacia, an agar, alginic acid, a carbomer, a dextrin, a gelatin, a veegum, a gellan gum, a sodium alginate, a methylcellulose, a hydroxyethyl cellulose, a hydroxypropyl cellulose, a hydroxypropylmethyl cellulose, a hydroxypropyl starch, a maltodextrin, a methylcellulose, a modified starch, a pectin, a poloxamer, a polycarbophil, a polyethylene glycol, a polyvinyl acetate, a poly(vinyl alcohol), a potassium alginate, a polyvinyl pyrrolidone, a pregelatinized starch, a propylene glycol alginate, a sodium alginate, a carboxymethyl cellulose, an alkali metal salt of a carboxymethyl cellulose, a microcrystalline cellulose, a gum arabic, a karaya gum, a sterculia gum, a tragacanth, a xanthan gum, a bentonite, a carageenan, a guar gum, a colloidal silicon dioxide, or a combination thereof, in an amount of from about 0.1 mg/mL to about 100 mg/mL.

12. The liquid oral pharmaceutical composition of claim 1, wherein the pharmaceutically acceptable excipient further comprises a viscosity modifying agent comprising an acacia, an agar, alginic acid, a carbomer, a dextrin, a gelatin, a veegum, a gellan gum, a sodium alginate, a methylcellulose, a hydroxyethyl cellulose, a hydroxypropyl cellulose, a hydroxypropylmethyl cellulose, a hydroxypropyl starch, a maltodextrin, a methylcellulose, a modified starch, a pectin, a poloxamer, a polycarbophil, a polyethylene glycol, a polyvinyl acetate, a poly (vinyl alcohol), a potassium alginate, a polyvinyl pyrrolidone, a pregelatinized starch, a propylene glycol alginate, a sodium alginate, a carboxymethyl cellulose, an alkali metal salt of a carboxymethyl cellulose, a microcrystalline cellulose, a gum arabic, a karaya gum, a sterculia gum, a tragacanth, a xanthan gum, a bentonite, a carageenan, a guar gum, a colloidal silicon dioxide, or a combination thereof, in an amount of from about 1 mg/mL to about 20 mg/mL.

13. The liquid oral pharmaceutical composition of claim 1, wherein the pharmaceutically acceptable excipient further comprises an anti-foaming agent comprising a simethicone, a simethicone emulsion, an organic phosphate, a paraffin oil, a stearate, a glycol, or a combination thereof, in an amount of from about 0.1 mg/mL to about 100 mg/mL.

14. The liquid oral pharmaceutical composition of claim 1, wherein the pharmaceutically acceptable excipient further comprises a pH adjusting agent, a pH modifying agent, or a combination thereof comprising acetic acid, adipic acid, ammonium carbonate, ammonium hydroxide, ammonium phosphate, boric acid, citric acid, diethanolamine, fumaric acid, hydrochloric acid, malic acid, nitric acid, propionic acid, potassium acetate, potassium bicarbonate, potassium citrate, potassium metaphosphate, potassium phosphate, sodium acetate, sodium bicarbonate, sodium borate, sodium carbonate, sodium citrate, sodium glycolate, sodium hydroxide, sodium lactate, sodium phosphate, sodium propionate, succinic acid, sulfuric acid, tartaric acid, triethylamine, triethanolamine, tromethamine, trolamine, or a combination thereof.

15. The liquid oral pharmaceutical composition of claim 1, wherein the pharmaceutically acceptable excipient comprises a pH adjusting agent, a pH modifying agent, or a combination thereof, wherein the pH modifying agent comprises acetic acid, adipic acid, ammonium carbonate, ammonium hydroxide, ammonium phosphate, boric acid, citric acid, diethanolamine, fumaric acid, hydrochloric acid, malic acid, nitric acid, propionic acid, potassium acetate, potassium bicarbonate, potassium citrate, potassium metaphosphate, potassium phosphate, sodium acetate, sodium bicarbonate, sodium borate, sodium carbonate, sodium citrate, sodium glycolate, sodium hydroxide, sodium lactate, sodium phosphate, sodium propionate, succinic acid, sulfuric acid, tartaric acid, triethylamine, triethanolamine, tromethamine, trolamine, or a combination thereof, in an amount of from about 0.01 M to about 0.1 M.

16. The liquid oral pharmaceutical composition of claim 1, wherein the pharmaceutically acceptable excipient further comprises a surfactant comprising a sodium lauryl sulfate, a docusate sodium, a cocamidopropyl amino betaine, a polyoxyethylene sorbitan fatty acid ester, a polyoxyethylene 15 hydroxystearate, a polyoxyethylene castor oil derivative, a polyoxyethylene stearate, a sorbitan fatty acid ester, a polyoxyethylene alkyl ether, a polyoxyethylene nonylphenol ether, or a combination thereof, in an amount of: (i) from 0.1 mg/mL to about 100 mg/mL.

17. The liquid oral pharmaceutical composition of claim 1, wherein the pharmaceutically acceptable excipient further comprises a surfactant comprising a sodium lauryl sulfate, a docusate sodium, a cocamidopropyl amino betaine, a polyoxyethylene sorbitan fatty acid ester, a polyoxyethylene 15 hydroxystearate, a polyoxyethylene castor oil derivative, a polyoxyethylene stearate, a sorbitan fatty acid ester, a polyoxyethylene alkyl ether, a polyoxyethylene nonylphenol ether, or a combination thereof, in an amount of from about 0.1 mg/mL to about 1 mg/mL.

18. The liquid oral pharmaceutical composition of claim 1,
wherein the preservative is present in an amount of: (i) from about 0.1 mg/mL to about 2.4 mg/mL or (ii) about 2.4 mg/mL; the sweetener is present in an amount of: (i) from about 0.1 mg/mL to about 6 mg/mL, (ii) from about 0.1 mg/mL to about 1 mg/mL, or (iii) about 1 mg/mL; and the flavorant is present in an amount of about 0.1 mg/mL.

19. The liquid oral pharmaceutical composition of claim 1, wherein the pharmaceutically acceptable excipient further comprises a viscosity modifying agent, an anti-foaming agent, a pH modifying agent, a pH adjusting agent, a surfactant, or a combination thereof.

20. The liquid oral pharmaceutical composition of claim 1,
wherein the wetting agent is present in an amount of from about 100 mg/mL to about 800 mg/mL and
wherein the pharmaceutically acceptable excipient further comprises
a viscosity modifying agent in an amount of from about 0.1 mg/mL to about 100 mg/mL,
an anti-foaming agent in an amount of from about 0.1 mg/mL to about 100 mg/mL,
a pH modifying agent in an amount of from about 0.01 M to about 0.5 M,
a surfactant in an amount of from about 0.1 mg/mL to about 100 mg/mL, or a combination thereof.

21. The liquid oral pharmaceutical composition of claim 1,
wherein the wetting agent is present in an amount of about 100 mg/mL to about 700 mg/mL, the preservative is present in an amount of from about 0.1 mg/mL to about 2.4 mg/mL, the sweetener is present in an amount of from about 0.1 mg/mL to about 6 mg/mL, and the flavorant in an amount of from about 0.1 mg/mL to about 50 mg/mL, and
wherein the pharmaceutically acceptable excipient further comprises
a viscosity modifying agent in an amount of from about 1 mg/mL to about 20 mg/mL,
an anti-foaming agent in an amount of from about 0.1 mg/mL to about 0.5 mg/mL,
a pH modifying agent in an amount of from about 0.01 M to about 0.1 M,
a surfactant in an amount of from about 0.1 mg/mL to about 1 mg/mL,
or a combination thereof.

22. The liquid oral pharmaceutical composition of claim 1,
wherein the wetting agent is present in an amount of from about 100 mg/mL to about 700 mg/mL, the preservative is present in an amount of from about 0.1 mg/mL to about 2.4 mg/mL, the sweetener is present in an amount of from about 0.1 mg/mL to about 6 mg/mL, and the flavorant is present in an amount of from about 0.1 mg/mL to about 50 mg/mL;
wherein the pharmaceutically acceptable excipient further comprises
a viscosity modifying agent in an amount of from about 1 mg/mL to about 20 mg/mL,
an anti-foaming agent in an amount of from about 0.1 mg/mL to about 0.5 mg/mL,
a pH modifying agent in an amount of from about 0.01 M to about 0.1 M,
a surfactant in an amount of from about 0.1 mg/mL to about 1 mg/mL; and
wherein the liquid oral pharmaceutical composition has a pH of from about 4 to about 6.

23. The liquid oral pharmaceutical composition of claim 1,
wherein the wetting agent is present in an amount of from about 200 mg/mL to about 600 mg/mL, the preservative is present in an amount of from about 0.1 mg/mL to about 2.4 mg/mL, the sweetener is present in an amount of from about 0.1 mg/mL to about 6 mg/mL, and the flavorant is present in an amount of from about 0.1 mg/mL to about 50 mg/mL; and
wherein the pharmaceutically acceptable excipient further comprises
a viscosity modifying agent in an amount of from about 1 mg/mL to about 6 mg/mL,
an anti-foaming agent in an amount of from about 0.1 mg/mL to about 0.5 mg/mL,
a pH modifying agent in an amount of from about 0.01 M to about 0.1 M,
a surfactant in an amount of from about 0.1 mg/mL to about 1 mg/mL,
or a combination thereof.

24. The liquid oral pharmaceutical composition of claim 1,
wherein the wetting agent is present in an amount of from about 200 mg/mL to about 600 mg/mL, the preservative is present in an amount of from about 0.1 mg/mL to about 2.4 mg/mL, the sweetener is present in an amount of from about 0.1 mg/mL to about 6 mg/mL, and the flavorant in an amount of from about 0.1 mg/mL to about 50 mg/mL; and
wherein the pharmaceutically acceptable excipient further comprises
a viscosity modifying agent in an amount of from about 1 mg/mL to about 6 mg/mL,
an anti-foaming agent in an amount of from about 0.1 mg/mL to about 0.5 mg/mL,
a pH modifying agent in an amount of from about 0.01 M to about 0.1 M, and
a surfactant in an amount of from about 0.1 mg/mL to about 1 mg/mL.

25. The liquid oral pharmaceutical composition of claim 1,
wherein the wetting agent comprises glycerin in an amount of from about 200 mg/mL to about 600 mg/mL, the preservative comprises benzoic acid or a salt thereof in an amount of from about 0.1 mg/mL to about 2.4 mg/mL, the sweetener comprises sucralose in an amount of from about 0.1 mg/mL to about 6 mg/mL, and the flavorant is present in an amount of from about 0.1 mg/mL to about 50 mg/mL; and
wherein the pharmaceutically acceptable excipient further comprises
a viscosity modifying agent comprising xanthan gum in an amount of from about 1 mg/mL to about 3 mg/mL,
an anti-foaming agent comprising a 30% simethicone emulsion in an amount of from about 0.1 mg/mL to about 0.5 mg/mL,
a pH modifying agent comprising a citrate buffer, a phosphate buffer, or a combination thereof in an amount of from about 0.01 M to about 0.1 M, and
a surfactant comprising a polyoxyethylene sorbitan fatty acid ester in an amount of from about 0.1 mg/mL to about 1 mg/mL.

26. The liquid oral pharmaceutical composition of claim 1,
wherein the wetting agent comprises glycerin in an amount of about 400 mg/mL, the preservative comprises benzoic acid or a salt thereof in an amount of from about 0.1 mg/mL to about 2.4 mg/mL, the sweetener comprises sucralose in an amount of from about 0.1 mg/mL to about 1 mg/mL, and the flavorant is present in an amount of about 0.1 mg/mL;
wherein the pharmaceutically acceptable excipient further comprises
a viscosity modifying agent comprising xanthan gum in an amount of from about 2 mg/mL to about 3 mg/mL,
an anti-foaming agent comprising a 30% simethicone emulsion in an amount of about 0.5 mg/mL,
a pH modifying agent comprising a citrate buffer, a phosphate buffer, or a combination thereof in an amount of from about 0.03 M,
a surfactant comprising a polyoxyethylene sorbitan fatty acid ester in an amount of from about 0.1 mg/mL to about 1 mg/mL,
wherein the liquid oral pharmaceutical composition has a pH of from about 4 to about 6.

27. A method for the treatment of a condition, which comprises administering to a human patient in need thereof a therapeutically effective amount of the liquid oral pharmaceutical composition of claim 1, wherein said condition is selected from the group consisting of pulmonary arterial hypertension, erectile dysfunction, benign prostatic hyperplasia, and a combination thereof.

28. A method for the treatment of a condition, which comprises administering to a human patient in need thereof a therapeutically effective amount of the liquid oral pharmaceutical composition of claim 1, wherein said condition is pulmonary arterial hypertension.

29. A method for the treatment of a condition, which comprises administering to a human patient in need thereof a therapeutically effective amount of the liquid oral pharmaceutical composition of claim 1, wherein said condition is erectile dysfunction.

30. A method for the treatment of a condition, which comprises administering to a human patient in need thereof a therapeutically effective amount of the liquid oral pharmaceutical composition of claim 1, wherein said condition is benign prostatic hyperplasia.

\* \* \* \* \*